US012186200B2

(12) United States Patent
Sack

(10) Patent No.: US 12,186,200 B2
(45) Date of Patent: *Jan. 7, 2025

(54) IMPLANT WITH IMPROVED BONE CONTACT

(71) Applicant: Institute for Musculoskeletal Science and Education, Ltd., King of Prussia, PA (US)

(72) Inventor: James A. Sack, Wayne, PA (US)

(73) Assignee: Institute for Musculoskeletal Science and Education, Ltd., King of Prussia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/491,186

(22) Filed: Oct. 20, 2023

(65) Prior Publication Data

US 2024/0050238 A1      Feb. 15, 2024

Related U.S. Application Data

(63) Continuation of application No. 16/995,192, filed on Aug. 17, 2020, now Pat. No. 11,793,652, which is a
(Continued)

(51) Int. Cl.
*A61F 2/44*  (2006.01)
*A61F 2/28*  (2006.01)
(Continued)

(52) U.S. Cl.
CPC .......... *A61F 2/4455* (2013.01); *A61F 2/2846* (2013.01); *A61F 2/30767* (2013.01);
(Continued)

(58) Field of Classification Search
CPC .......... A61F 2/4455–2/447; A61F 2002/3092; A61F 2002/3093; A61F 2250/0026
See application file for complete search history.

(56) References Cited

U.S. PATENT DOCUMENTS

| 3,720,959 A | 3/1973 | Hahn |
| 4,038,703 A | 8/1977 | Bokros |

(Continued)

FOREIGN PATENT DOCUMENTS

| CN | 101708138 | 5/2010 |
| CN | 103932841 | 7/2014 |

(Continued)

OTHER PUBLICATIONS

May 2017 in U.S. Appl. No. 15/141,655.
(Continued)

*Primary Examiner* — Julianna N Harvey
(74) *Attorney, Agent, or Firm* — Plumsea Law Group, LLC

(57) ABSTRACT

An intervertebral implant having an open lattice structure formed by a plurality of elongate struts, including a first strut and a second strut. In addition, the body includes a contact surface configured to confront a bone plate, the contact surface including a node defined by an intersection of the first strut and the second strut. The implant includes an enlarged contact member disposed at the node, wherein the enlarged contact member has a substantially flattened outer-facing surface forming part of the contact surface. In addition, the enlarged contact member has an outer perimeter edge that extends beyond the node, and at least a portion of the first strut and at least a portion of the second strut extend inward from the enlarged contact member toward a central core of the body.

20 Claims, 12 Drawing Sheets

Related U.S. Application Data continuation of application No. 15/820,125, filed on Nov. 21, 2017, now Pat. No. 10,744,001.

(51) Int. Cl.
*A61F 2/30* (2006.01)
*A61B 17/68* (2006.01)
*A61F 2/46* (2006.01)
*A61L 27/36* (2006.01)

(52) U.S. Cl.
CPC ..... *A61B 17/68* (2013.01); *A61F 2002/30062* (2013.01); *A61F 2002/30156* (2013.01); *A61F 2002/30224* (2013.01); *A61F 2002/30289* (2013.01); *A61F 2002/30593* (2013.01); *A61F 2002/3093* (2013.01); *A61F 2002/30985* (2013.01); *A61F 2002/4495* (2013.01); *A61F 2002/4629* (2013.01); *A61F 2250/0026* (2013.01); *A61L 27/3608* (2013.01)

(56) References Cited

U.S. PATENT DOCUMENTS

| | | |
|---|---|---|
| 4,309,777 A | 1/1982 | Patil |
| 4,759,769 A | 7/1988 | Hedman |
| 4,851,008 A | 7/1989 | Johnson |
| 4,889,685 A | 12/1989 | Shimamune |
| 4,917,704 A | 4/1990 | Frey |
| 4,961,740 A | 10/1990 | Ray et al. |
| 5,055,104 A | 10/1991 | Ray |
| 5,059,193 A | 10/1991 | Kuslich |
| 5,198,308 A | 3/1993 | Shetty et al. |
| 5,263,953 A | 11/1993 | Bagby |
| 5,306,310 A | 4/1994 | Siebels |
| 5,397,359 A | 3/1995 | Mittelmeier |
| 5,423,817 A | 6/1995 | Lin |
| 5,458,638 A | 10/1995 | Kuslich et al. |
| 5,571,185 A | 11/1996 | Schug |
| 5,571,192 A | 11/1996 | Schonhoffer |
| 5,607,424 A | 3/1997 | Tropiano |
| 5,609,635 A | 3/1997 | Michelson |
| 5,609,636 A | 3/1997 | Kohrs |
| 5,658,337 A | 8/1997 | Kohrs et al. |
| 5,709,683 A | 1/1998 | Bagby |
| 5,716,416 A | 2/1998 | Lin |
| D403,069 S | 12/1998 | Drewry et al. |
| 5,885,299 A | 3/1999 | Winslow |
| 5,888,223 A | 3/1999 | Bray, Jr. |
| 5,897,556 A | 4/1999 | Drewry et al. |
| 5,954,504 A | 9/1999 | Misch et al. |
| 5,968,098 A | 10/1999 | Winslow |
| 5,973,222 A | 10/1999 | Devanathan et al. |
| 6,010,502 A | 1/2000 | Bagby |
| 6,039,762 A | 3/2000 | McKay |
| 6,090,143 A | 7/2000 | Meriwether et al. |
| 6,102,948 A | 8/2000 | Brosnahan, III |
| 6,126,689 A | 10/2000 | Brett |
| 6,149,651 A | 11/2000 | Drewry et al. |
| 6,156,037 A | 12/2000 | LeHuec et al. |
| 6,200,348 B1 | 3/2001 | Biedermann et al. |
| 6,206,924 B1 * | 3/2001 | Timm ............... A61F 2/28 623/17.11 |
| 6,210,412 B1 | 4/2001 | Michelson |
| 6,371,987 B1 | 4/2002 | Weiland et al. |
| 6,428,575 B2 | 8/2002 | Koo et al. |
| 6,436,141 B2 | 8/2002 | Castro et al. |
| 6,464,727 B1 | 10/2002 | Sharkey |
| 6,468,309 B1 | 10/2002 | Lieberman |
| 6,494,883 B1 | 12/2002 | Ferree |
| 6,500,205 B1 | 12/2002 | Michelson |
| 6,520,996 B1 | 2/2003 | Manasas et al. |
| 6,527,805 B2 | 3/2003 | Studer et al. |
| 6,530,956 B1 | 3/2003 | Mansmann |
| 6,537,320 B1 | 3/2003 | Michelson |
| 6,558,423 B1 | 5/2003 | Michelson |
| 6,569,201 B2 | 5/2003 | Moumene |
| 6,582,431 B1 | 6/2003 | Ray |
| 6,582,467 B1 | 6/2003 | Teitelbaum et al. |
| 6,585,770 B1 | 7/2003 | White et al. |
| 6,616,695 B1 | 9/2003 | Crozet et al. |
| 6,666,888 B1 | 12/2003 | Jackson |
| 6,709,458 B2 | 3/2004 | Michelson |
| 6,716,245 B2 | 4/2004 | Pasquet |
| 6,758,849 B1 | 7/2004 | Michelson |
| 6,808,537 B2 | 10/2004 | Michelson |
| 6,846,327 B2 | 1/2005 | Khandkar et al. |
| 6,849,093 B2 | 2/2005 | Michelson |
| 6,863,689 B2 | 3/2005 | Ralph et al. |
| 6,890,355 B2 | 5/2005 | Michelson |
| 6,923,810 B1 | 8/2005 | Michelson |
| 6,962,606 B2 | 11/2005 | Michelson |
| 6,997,953 B2 | 2/2006 | Chung et al. |
| 7,135,043 B2 | 11/2006 | Nakahara et al. |
| 7,141,068 B2 | 11/2006 | Ross et al. |
| 7,153,325 B2 | 12/2006 | Kim et al. |
| 7,186,267 B2 | 3/2007 | Aston et al. |
| 7,241,313 B2 | 7/2007 | Unwin et al. |
| 7,261,739 B2 | 8/2007 | Ralph |
| 7,297,162 B2 | 11/2007 | Mujwid |
| 7,341,601 B2 | 3/2008 | Eisermann et al. |
| 7,361,193 B2 | 4/2008 | Frey |
| 7,410,501 B2 | 8/2008 | Michelson |
| 7,429,270 B2 | 9/2008 | Baumgartner et al. |
| 7,435,261 B1 | 10/2008 | Castro |
| 7,452,369 B2 | 11/2008 | Barry |
| 7,465,318 B2 | 12/2008 | Sennett |
| 7,485,134 B2 | 2/2009 | Simonson |
| 7,527,649 B1 | 5/2009 | Blain |
| 7,534,254 B1 | 5/2009 | Michelson |
| 7,537,603 B2 | 5/2009 | Huebner et al. |
| 7,537,616 B1 | 5/2009 | Branch et al. |
| 7,575,598 B2 | 8/2009 | Albert |
| 7,611,217 B2 | 11/2009 | Shamoun et al. |
| 7,621,952 B2 | 11/2009 | Truckai et al. |
| 7,621,953 B2 | 11/2009 | Braddock, Jr. et al. |
| 7,628,814 B2 | 12/2009 | Studer et al. |
| 7,645,475 B2 | 1/2010 | Prewett |
| 7,655,043 B2 | 2/2010 | Peterman et al. |
| 7,794,500 B2 | 9/2010 | Felix |
| 7,799,056 B2 | 9/2010 | Sankaran |
| 7,803,191 B2 | 9/2010 | Biedermann et al. |
| 7,815,665 B2 | 10/2010 | Jahng |
| 7,846,207 B2 | 12/2010 | Lechmann |
| 7,875,075 B2 | 1/2011 | Schwab |
| 7,879,100 B2 | 2/2011 | Denoziere |
| 7,879,103 B2 | 2/2011 | Gertzman et al. |
| 7,935,149 B2 | 5/2011 | Michelson |
| 8,016,887 B1 | 9/2011 | Castro |
| 8,021,424 B2 | 9/2011 | Beger et al. |
| 8,021,426 B2 | 9/2011 | Segal et al. |
| 8,062,365 B2 | 11/2011 | Schwab |
| 8,092,536 B2 | 1/2012 | Ahrens et al. |
| 8,142,507 B2 | 3/2012 | McGuckin, Jr. |
| 8,152,849 B2 | 4/2012 | Biedermann et al. |
| 8,182,538 B2 | 5/2012 | O'Neil et al. |
| 8,226,718 B2 | 7/2012 | Castro |
| 8,241,363 B2 | 8/2012 | Sommerich et al. |
| 8,246,683 B2 | 8/2012 | Castro |
| 8,252,059 B2 | 8/2012 | Overes et al. |
| 8,298,286 B2 | 10/2012 | Trieu |
| 8,303,879 B2 | 11/2012 | Bertele et al. |
| 8,343,224 B2 | 1/2013 | Lynn |
| 8,361,149 B2 | 1/2013 | Castro |
| 8,366,777 B2 | 2/2013 | Matthis et al. |
| D681,204 S | 4/2013 | Farris et al. |
| 8,414,654 B1 | 4/2013 | Ganey |
| 8,414,820 B2 | 4/2013 | Bertele et al. |
| 8,430,930 B2 | 4/2013 | Hunt |
| D681,812 S | 5/2013 | Farris et al. |
| 8,435,300 B2 | 5/2013 | Messerli et al. |
| 8,454,700 B2 | 6/2013 | Lemoine et al. |
| 8,475,533 B1 | 7/2013 | Castro |
| 8,529,628 B2 | 9/2013 | Marino et al. |

(56) References Cited

U.S. PATENT DOCUMENTS

| | | |
|---|---|---|
| 8,540,769 B2 | 9/2013 | Janowski |
| 8,551,173 B2 | 10/2013 | Lechmann et al. |
| 8,556,978 B2 | 10/2013 | Schaller |
| 8,568,413 B2 | 10/2013 | Mazur et al. |
| 8,613,769 B2 | 12/2013 | Sears et al. |
| 8,623,090 B2 | 1/2014 | Butler |
| 8,673,006 B2 | 3/2014 | Castro |
| 8,700,198 B2 | 4/2014 | Conway et al. |
| 8,702,808 B2 | 4/2014 | Teoh et al. |
| 8,709,042 B2 | 4/2014 | Greenhalgh et al. |
| 8,728,160 B2 | 5/2014 | Globerman |
| 8,740,981 B2 | 6/2014 | Tornier et al. |
| 8,771,357 B2 | 7/2014 | Biedermann et al. |
| 8,771,368 B2 | 7/2014 | McKay |
| 8,795,362 B2 | 8/2014 | Anderson et al. |
| 8,801,787 B2 | 8/2014 | Schaller |
| 8,808,376 B2 | 8/2014 | Schaller |
| 8,808,725 B2 | 8/2014 | Altschuler et al. |
| 8,840,614 B2 | 9/2014 | Mikhail et al. |
| 8,864,831 B2 | 10/2014 | Lee et al. |
| 8,894,661 B2 | 11/2014 | McDevitt |
| 8,900,310 B2 | 12/2014 | Carlson |
| 8,900,312 B2 | 12/2014 | McLean et al. |
| 8,932,356 B2 | 1/2015 | Kraus |
| 8,940,050 B2 | 1/2015 | Laurence |
| 8,940,052 B2 | 1/2015 | Lechmann et al. |
| 8,951,300 B2 | 2/2015 | Parrish |
| 8,986,383 B2 | 3/2015 | Castro |
| 9,011,499 B1 | 4/2015 | Kiester |
| 9,039,766 B1 | 5/2015 | Fonte |
| 9,060,876 B1 | 6/2015 | To |
| 9,101,491 B2 | 8/2015 | Rodgers |
| D739,935 S | 9/2015 | Blain et al. |
| 9,138,301 B2 | 9/2015 | Kita et al. |
| 9,155,819 B2 | 10/2015 | Fonte et al. |
| 9,186,252 B2 | 11/2015 | Leibinger |
| 9,186,257 B2 | 11/2015 | Geisler et al. |
| 9,220,518 B2 | 12/2015 | Neal et al. |
| 9,237,958 B2 | 1/2016 | Duggal et al. |
| 9,247,970 B2 | 2/2016 | Teisen |
| 9,254,199 B2 | 2/2016 | Biedermann et al. |
| 9,271,765 B2 | 3/2016 | Blain |
| 9,271,771 B2 | 3/2016 | Mathieu et al. |
| 9,271,845 B2 | 3/2016 | Hunt et al. |
| 9,289,308 B2 | 3/2016 | Marino et al. |
| 9,289,312 B2 | 3/2016 | Davenport et al. |
| 9,295,562 B2 | 3/2016 | Lechmann et al. |
| 9,364,330 B2 | 6/2016 | Lindsey et al. |
| 9,364,339 B2 | 6/2016 | Mayer |
| 9,402,733 B1 | 8/2016 | To et al. |
| 9,408,651 B2 | 8/2016 | Sennett et al. |
| 9,421,108 B2 | 8/2016 | Hunt |
| 9,427,328 B2 | 8/2016 | Drochner |
| 9,433,510 B2 | 9/2016 | Lechmann et al. |
| 9,433,511 B2 | 9/2016 | Bagga et al. |
| 9,439,779 B2 | 9/2016 | Zhang et al. |
| 9,439,948 B2 | 9/2016 | Lin et al. |
| 9,451,940 B2 | 9/2016 | Spann |
| 9,452,056 B2 | 9/2016 | Early et al. |
| 9,452,064 B2 | 9/2016 | Trautwein et al. |
| 9,456,901 B2 | 10/2016 | Jones et al. |
| 9,456,907 B1 | 10/2016 | Castro |
| 9,474,624 B1 | 10/2016 | Ahn |
| 9,517,095 B2 | 12/2016 | Vaidya |
| 9,522,028 B2 | 12/2016 | Warren et al. |
| 9,526,548 B2 | 12/2016 | Asfora |
| 9,545,317 B2 | 1/2017 | Hunt |
| 9,549,823 B2 | 1/2017 | Hunt et al. |
| 9,554,914 B2 | 1/2017 | Taylor et al. |
| 9,561,117 B2 | 2/2017 | Lechmann et al. |
| 9,566,095 B2 | 2/2017 | Lorio |
| 9,566,100 B2 | 2/2017 | Asfora |
| 9,572,669 B2 | 2/2017 | Hunt et al. |
| 9,597,197 B2 | 3/2017 | Lechmann et al. |
| 9,603,613 B2 | 3/2017 | Schoenefeld et al. |
| 9,622,880 B2 | 4/2017 | Dunworth et al. |
| 9,629,727 B2 | 4/2017 | Baynham |
| 9,636,226 B2 | 5/2017 | Hunt |
| 9,649,200 B2 | 5/2017 | Wickham |
| 9,662,128 B2 | 5/2017 | Reiley |
| 9,662,157 B2 | 5/2017 | Schneider et al. |
| 9,662,158 B2 | 5/2017 | Reiley |
| 9,662,224 B2 | 5/2017 | Weiman et al. |
| 9,662,226 B2 | 5/2017 | Wickham |
| 9,668,781 B2 | 6/2017 | Stark |
| 9,675,394 B2 | 6/2017 | Reiley |
| 9,700,356 B2 | 7/2017 | Donner et al. |
| 9,744,051 B2 | 8/2017 | Biedermann et al. |
| 9,757,235 B2 | 9/2017 | Hunt et al. |
| 9,782,270 B2 | 10/2017 | Wickham |
| 9,788,967 B2 | 10/2017 | Jo |
| 9,814,578 B1 | 11/2017 | Gotfried |
| 9,907,670 B2 | 3/2018 | DeRidder et al. |
| 9,918,849 B2 | 3/2018 | Morris et al. |
| 9,931,209 B2 | 4/2018 | Gotfried |
| 9,987,051 B2 | 6/2018 | Nunley et al. |
| 9,987,137 B2 | 6/2018 | Hunt et al. |
| 9,999,516 B2 | 6/2018 | Hunt |
| 10,004,546 B2 | 6/2018 | Gotfried |
| 10,016,279 B1 | 7/2018 | Castro |
| 10,058,433 B2 | 8/2018 | Lechmann et al. |
| 10,064,737 B2 | 9/2018 | Tsai et al. |
| 10,098,754 B2 | 10/2018 | Larsson |
| 10,117,746 B2 | 11/2018 | Cordaro |
| 10,143,569 B2 | 12/2018 | Weiman et al. |
| 10,154,913 B2 | 12/2018 | Steinmann et al. |
| 10,159,580 B2 | 12/2018 | Guizzardi et al. |
| 10,182,923 B2 | 1/2019 | Willis et al. |
| 10,194,962 B2 | 2/2019 | Schneider et al. |
| 10,195,524 B2 | 2/2019 | DeRidder et al. |
| 10,213,317 B2 | 2/2019 | Bishop et al. |
| 10,226,357 B2 | 3/2019 | Ries |
| 10,265,189 B2 | 4/2019 | Melkent et al. |
| 10,271,958 B2 | 4/2019 | Schaufler et al. |
| 10,278,833 B2 | 5/2019 | Howard et al. |
| 10,278,834 B2 | 5/2019 | Howard et al. |
| 10,357,277 B2 | 7/2019 | Patel et al. |
| 10,357,377 B2 | 7/2019 | Nyahay et al. |
| 10,368,997 B2 | 8/2019 | Jones et al. |
| 10,369,009 B2 | 8/2019 | Joly et al. |
| 10,383,740 B2 | 8/2019 | Duarte |
| 10,413,427 B2 | 9/2019 | Trieu |
| 10,433,977 B2 | 10/2019 | Lechmann et al. |
| 10,433,979 B2 | 10/2019 | Morris et al. |
| 10,449,051 B2 | 10/2019 | Hamzey et al. |
| 10,449,055 B2 | 10/2019 | McJunkin |
| 10,449,058 B2 | 10/2019 | Lechmann et al. |
| 10,478,312 B2 | 11/2019 | McShane, III et al. |
| D870,288 S | 12/2019 | Dang et al. |
| 10,492,921 B2 | 12/2019 | McShane, III et al. |
| 10,507,118 B2 | 12/2019 | Afzal |
| 10,512,549 B2 | 12/2019 | Bishop et al. |
| 10,517,739 B2 | 12/2019 | Ryan |
| 10,524,926 B2 | 1/2020 | Jasinski |
| 10,524,927 B2 | 1/2020 | Ryan |
| 10,524,929 B2 | 1/2020 | Shoshtaev |
| 10,525,688 B2 | 1/2020 | O'Neill et al. |
| 10,531,962 B2 | 1/2020 | Petersheim et al. |
| 10,537,666 B2 | 1/2020 | Paddock |
| 10,555,819 B2 | 2/2020 | Miccio |
| 10,561,456 B2 | 2/2020 | Cawley et al. |
| 10,575,965 B2 | 3/2020 | Kim et al. |
| 10,588,755 B2 | 3/2020 | Vogt et al. |
| 10,617,532 B2 | 4/2020 | Mazur et al. |
| 10,624,760 B2 | 4/2020 | Mirda et al. |
| 10,660,763 B2 | 5/2020 | Wilson et al. |
| 10,660,764 B2 | 5/2020 | Maglaras et al. |
| 10,667,924 B2 | 6/2020 | Nyahay et al. |
| 10,675,158 B2 | 6/2020 | Unger et al. |
| 10,675,385 B2 | 6/2020 | Barbas et al. |
| 10,682,238 B2 | 6/2020 | Petersheim et al. |
| 10,695,192 B2 | 6/2020 | Bishop et al. |
| 10,709,570 B2 | 7/2020 | Stauffer et al. |
| 10,716,678 B2 | 7/2020 | Stampfli et al. |

(56) References Cited

U.S. PATENT DOCUMENTS

| | | |
|---|---|---|
| 10,722,378 B2 | 7/2020 | Davis et al. |
| 10,744,001 B2 | 8/2020 | Sack |
| 10,744,003 B2 | 8/2020 | Ryan et al. |
| 10,765,530 B2 | 9/2020 | Steinmann et al. |
| 10,772,732 B1 | 9/2020 | Miller et al. |
| D898,197 S | 10/2020 | Cain |
| 10,835,388 B2 | 11/2020 | Milz et al. |
| 10,849,756 B2 | 12/2020 | Hunt et al. |
| 10,856,999 B2 | 12/2020 | Bishop et al. |
| 10,893,945 B2 | 1/2021 | Duarte |
| 10,940,019 B2 | 3/2021 | Vishnubhotla et al. |
| D920,515 S | 5/2021 | Miller et al. |
| D920,516 S | 5/2021 | Miller et al. |
| 11,026,798 B1 | 6/2021 | Miller et al. |
| 11,033,394 B2 | 6/2021 | Hamzey et al. |
| 11,065,039 B2 | 7/2021 | McCormack |
| 11,147,679 B2 | 10/2021 | Kowalczyk et al. |
| 11,160,668 B2 | 11/2021 | Nyahay et al. |
| D942,011 S | 1/2022 | Cain |
| 11,213,405 B2 | 1/2022 | Bishop et al. |
| D942,623 S | 2/2022 | Cain |
| D942,624 S | 2/2022 | Cain |
| D944,400 S | 2/2022 | Cain |
| 11,273,048 B2 | 3/2022 | Cain et al. |
| 11,452,611 B2 | 9/2022 | McShane, III et al. |
| 11,793,652 B2 * | 10/2023 | Sack .................. A61F 2/30767 |
| 2001/0014826 A1 | 8/2001 | Biedermann et al. |
| 2001/0032018 A1 | 10/2001 | Castro et al. |
| 2002/0052656 A1 | 5/2002 | Michelson |
| 2002/0120334 A1 | 8/2002 | Crozet |
| 2002/0123750 A1 | 9/2002 | Eisermann et al. |
| 2002/0183847 A1 | 12/2002 | Lieberman |
| 2003/0003127 A1 | 1/2003 | Brown et al. |
| 2003/0060825 A1 | 3/2003 | Alfaro |
| 2003/0078660 A1 | 4/2003 | Clifford et al. |
| 2003/0083746 A1 | 5/2003 | Kuslich |
| 2003/0109928 A1 | 6/2003 | Pasquet |
| 2003/0181913 A1 | 9/2003 | Lieberman |
| 2003/0236571 A1 | 12/2003 | Ralph |
| 2004/0059419 A1 | 3/2004 | Michelson |
| 2004/0082953 A1 | 4/2004 | Petit |
| 2004/0122518 A1 | 6/2004 | Rhoda |
| 2004/0172130 A1 | 9/2004 | Nakahara |
| 2004/0193270 A1 | 9/2004 | DiMauro et al. |
| 2004/0210312 A1 | 10/2004 | Neumann |
| 2004/0225361 A1 | 11/2004 | Glenn et al. |
| 2005/0015154 A1 | 1/2005 | Lindsey et al. |
| 2005/0027364 A1 | 2/2005 | Kim |
| 2005/0143733 A1 | 6/2005 | Petit |
| 2005/0177238 A1 | 8/2005 | Khandkar et al. |
| 2005/0222681 A1 | 10/2005 | Richley et al. |
| 2005/0278027 A1 | 12/2005 | Hyde, Jr. |
| 2005/0278028 A1 | 12/2005 | Mujwid |
| 2006/0041262 A1 | 2/2006 | Calvert et al. |
| 2006/0052872 A1 | 3/2006 | Studer |
| 2006/0052873 A1 | 3/2006 | Buck |
| 2006/0058881 A1 | 3/2006 | Trieu |
| 2006/0100706 A1 | 5/2006 | Shadduck et al. |
| 2006/0147332 A1 | 7/2006 | Jones et al. |
| 2006/0212118 A1 | 9/2006 | Abernathie |
| 2006/0217806 A1 | 9/2006 | Peterman |
| 2006/0293753 A1 | 12/2006 | Thramann |
| 2007/0027544 A1 | 2/2007 | McCord et al. |
| 2007/0179610 A1 | 8/2007 | Biedermann et al. |
| 2007/0198090 A1 | 8/2007 | Abdou |
| 2007/0260324 A1 | 11/2007 | Joshi et al. |
| 2008/0071356 A1 | 3/2008 | Greenhalgh |
| 2008/0167686 A1 | 7/2008 | Trieu |
| 2008/0183204 A1 | 7/2008 | Greenhalgh et al. |
| 2008/0255666 A1 | 10/2008 | Fisher |
| 2008/0288083 A1 | 11/2008 | Axelsson et al. |
| 2008/0300602 A1 | 12/2008 | Schmitt et al. |
| 2008/0306595 A1 | 12/2008 | McLeod et al. |
| 2008/0312742 A1 | 12/2008 | Abernathie |
| 2009/0030520 A1 | 1/2009 | Biedermann |
| 2009/0036985 A1 | 2/2009 | Whiting |
| 2009/0048675 A1 | 2/2009 | Bhatnagar et al. |
| 2009/0048678 A1 | 2/2009 | Saal et al. |
| 2009/0062917 A1 | 3/2009 | Foley et al. |
| 2009/0112321 A1 | 4/2009 | Kitchen |
| 2009/0149958 A1 | 6/2009 | Prewett et al. |
| 2009/0248162 A1 | 10/2009 | Peckham |
| 2010/0016974 A1 | 1/2010 | Janowski |
| 2010/0036498 A1 | 2/2010 | McDevitt |
| 2010/0057216 A1 | 3/2010 | Gannoe et al. |
| 2010/0137990 A1 | 6/2010 | Apatsidis |
| 2010/0152856 A1 | 6/2010 | Overes |
| 2010/0161061 A1 | 6/2010 | Hunt |
| 2010/0185292 A1 | 7/2010 | Hochschuler |
| 2010/0228299 A1 | 9/2010 | Zrinski et al. |
| 2010/0286778 A1 | 11/2010 | Eisermann et al. |
| 2011/0015741 A1 | 1/2011 | Melkent et al. |
| 2011/0029085 A1 | 2/2011 | Hynes |
| 2011/0035019 A1 | 2/2011 | Goswami et al. |
| 2011/0066192 A1 | 3/2011 | Frasier et al. |
| 2011/0166660 A1 | 7/2011 | Laurence |
| 2011/0190888 A1 | 8/2011 | Bertele |
| 2011/0190895 A1 | 8/2011 | Segal et al. |
| 2011/0208311 A1 | 8/2011 | Janowski |
| 2011/0230970 A1 | 9/2011 | Lynn |
| 2011/0245926 A1 | 10/2011 | Kitchen |
| 2011/0270401 A1 | 11/2011 | McKay |
| 2011/0301709 A1 | 12/2011 | Kraus et al. |
| 2011/0313528 A1 | 12/2011 | Laubert |
| 2011/0313532 A1 * | 12/2011 | Hunt ........................ A61F 2/46 623/18.11 |
| 2012/0010472 A1 | 1/2012 | Spann |
| 2012/0010717 A1 | 1/2012 | Spann |
| 2012/0150300 A1 | 6/2012 | Nihalani |
| 2012/0158143 A1 | 6/2012 | Shapiro |
| 2012/0191188 A1 | 7/2012 | Huang |
| 2012/0191189 A1 | 7/2012 | Huang |
| 2012/0239150 A1 | 9/2012 | Ullrich |
| 2012/0296431 A1 | 11/2012 | Kim |
| 2013/0030529 A1 * | 1/2013 | Hunt .................. A61F 2/30771 623/16.11 |
| 2013/0096685 A1 | 4/2013 | Ciupik |
| 2013/0116793 A1 | 5/2013 | Kloss |
| 2013/0123935 A1 | 5/2013 | Hunt et al. |
| 2013/0158672 A1 | 6/2013 | Hunt |
| 2013/0184826 A1 | 7/2013 | Thaiyananthan |
| 2013/0190880 A1 | 7/2013 | Schaller |
| 2013/0218282 A1 | 8/2013 | Hunt |
| 2013/0218288 A1 | 8/2013 | Fonte |
| 2013/0226300 A1 | 8/2013 | Chataigner |
| 2013/0304211 A1 | 11/2013 | Trautwein et al. |
| 2014/0018814 A1 | 1/2014 | Gillard et al. |
| 2014/0052260 A1 | 2/2014 | McKenny |
| 2014/0058513 A1 | 2/2014 | Gahman et al. |
| 2014/0107785 A1 | 4/2014 | Geisler |
| 2014/0107786 A1 | 4/2014 | Geisler et al. |
| 2014/0114418 A1 | 4/2014 | Landry |
| 2014/0121776 A1 * | 5/2014 | Hunt ...................... A61F 2/4202 623/17.16 |
| 2014/0142707 A1 | 5/2014 | Compton et al. |
| 2014/0172111 A1 | 6/2014 | Lang et al. |
| 2014/0195005 A1 | 7/2014 | McKay |
| 2014/0228956 A1 | 8/2014 | Weiman |
| 2014/0228960 A1 * | 8/2014 | Forterre .................. A61F 2/447 623/17.16 |
| 2014/0243980 A1 | 8/2014 | Sack et al. |
| 2014/0249631 A1 | 9/2014 | Weiman |
| 2014/0277457 A1 | 9/2014 | Yeung et al. |
| 2014/0277464 A1 | 9/2014 | Richter et al. |
| 2014/0277569 A1 | 9/2014 | Lange |
| 2014/0288649 A1 | 9/2014 | Hunt |
| 2014/0288650 A1 | 9/2014 | Hunt |
| 2014/0303736 A1 | 10/2014 | Roussouly |
| 2014/0303745 A1 | 10/2014 | Anderson et al. |
| 2014/0309743 A1 | 10/2014 | Falahee |
| 2014/0336771 A1 | 11/2014 | Zambiasi |
| 2014/0358246 A1 | 12/2014 | Levy et al. |
| 2015/0045903 A1 | 2/2015 | Neal |
| 2015/0112351 A1 | 4/2015 | Hsu |

(56) References Cited

U.S. PATENT DOCUMENTS

| | | |
|---|---|---|
| 2015/0127106 A1 | 5/2015 | Partee et al. |
| 2015/0173910 A1 | 6/2015 | Siegal |
| 2015/0223951 A1 | 8/2015 | Bae et al. |
| 2015/0282944 A1 | 10/2015 | Guizzardi et al. |
| 2016/0015437 A1 | 1/2016 | Elleby et al. |
| 2016/0022430 A1 | 1/2016 | Wickham |
| 2016/0081809 A1 | 3/2016 | Schneider et al. |
| 2016/0166284 A1 | 6/2016 | Hacking et al. |
| 2016/0184103 A1 | 6/2016 | Fonte et al. |
| 2016/0193057 A1 | 7/2016 | Rhoda |
| 2016/0206439 A1 | 7/2016 | To et al. |
| 2016/0206440 A1 | 7/2016 | DeRidder et al. |
| 2016/0262903 A1 | 9/2016 | West |
| 2016/0270920 A1 | 9/2016 | Dawson et al. |
| 2016/0287388 A1 | 10/2016 | Hunt et al. |
| 2016/0310294 A1 | 10/2016 | McConnell |
| 2016/0317320 A1 | 11/2016 | Ahn |
| 2016/0324656 A1 | 11/2016 | Morris et al. |
| 2016/0374727 A1 | 12/2016 | Greenhalgh et al. |
| 2017/0007409 A1 | 1/2017 | Mauldin et al. |
| 2017/0014235 A1 | 1/2017 | Jones et al. |
| 2017/0020685 A1 | 1/2017 | Geisler et al. |
| 2017/0042697 A1* | 2/2017 | McShane, III ........ A61F 2/4455 |
| 2017/0049488 A1 | 2/2017 | Vestgaarden |
| 2017/0095337 A1 | 4/2017 | Pasini et al. |
| 2017/0095352 A1 | 4/2017 | Bruffey |
| 2017/0100167 A1 | 4/2017 | Lange et al. |
| 2017/0135706 A1 | 5/2017 | Frey et al. |
| 2017/0135733 A1 | 5/2017 | Donner et al. |
| 2017/0143383 A1 | 5/2017 | Ingalhalikar et al. |
| 2017/0151005 A1 | 6/2017 | Warren et al. |
| 2017/0156740 A9 | 6/2017 | Stark |
| 2017/0156766 A1 | 6/2017 | Anderson et al. |
| 2017/0156878 A1 | 6/2017 | Tsai |
| 2017/0156879 A1 | 6/2017 | Janowski |
| 2017/0156880 A1 | 6/2017 | Halverson et al. |
| 2017/0164979 A1 | 6/2017 | Donner et al. |
| 2017/0181784 A1 | 6/2017 | Li |
| 2017/0182222 A1 | 6/2017 | Paddock |
| 2017/0196693 A1 | 7/2017 | Jurick et al. |
| 2017/0216034 A1 | 8/2017 | Daniel |
| 2017/0216035 A1 | 8/2017 | Hunt |
| 2017/0239064 A1 | 8/2017 | Cordaro |
| 2017/0239066 A1 | 8/2017 | Walsh et al. |
| 2017/0258606 A1* | 9/2017 | Afzal .................... A61F 2/4465 |
| 2017/0319353 A1 | 11/2017 | Greenhalgh et al. |
| 2017/0348107 A1 | 12/2017 | Lee et al. |
| 2017/0348115 A1 | 12/2017 | Greenhalgh |
| 2018/0064540 A1 | 3/2018 | Hunt et al. |
| 2018/0085230 A1 | 3/2018 | Hunt |
| 2018/0110626 A1 | 4/2018 | McShane, III et al. |
| 2018/0161477 A1 | 6/2018 | Nies |
| 2018/0221156 A1 | 8/2018 | Jones |
| 2018/0243104 A1 | 8/2018 | Garonzik |
| 2018/0256336 A1 | 9/2018 | Mueller et al. |
| 2018/0256352 A1 | 9/2018 | Nyahay et al. |
| 2018/0280139 A1 | 10/2018 | Jones |
| 2018/0289503 A1 | 10/2018 | Knapp |
| 2018/0296343 A1 | 10/2018 | Wei |
| 2018/0326493 A1 | 11/2018 | Gallagher et al. |
| 2018/0333272 A1 | 11/2018 | Mirda |
| 2018/0338838 A1 | 11/2018 | Cryder et al. |
| 2018/0368981 A1 | 12/2018 | Mattes et al. |
| 2018/0368991 A1 | 12/2018 | Levieux |
| 2019/0000636 A1 | 1/2019 | Kim et al. |
| 2019/0015209 A1 | 1/2019 | Seifert et al. |
| 2019/0038428 A1 | 2/2019 | Stauffer |
| 2019/0060079 A1 | 2/2019 | Unis et al. |
| 2019/0060083 A1 | 2/2019 | Weiman et al. |
| 2019/0076266 A1 | 3/2019 | Trudeau et al. |
| 2019/0083282 A1 | 3/2019 | Roeder et al. |
| 2019/0091027 A1 | 3/2019 | Asaad et al. |
| 2019/0133769 A1 | 5/2019 | Tetsworth et al. |
| 2019/0151109 A1 | 5/2019 | Arnin |
| 2019/0151113 A1 | 5/2019 | Sack |
| 2019/0159818 A1 | 5/2019 | Schneider et al. |
| 2019/0183653 A1* | 6/2019 | Gregersen ............... A61F 2/447 |
| 2019/0224023 A1 | 7/2019 | Howard et al. |
| 2019/0231554 A1* | 8/2019 | Bishop .................. A61F 2/4611 |
| 2019/0254840 A1 | 8/2019 | Gray et al. |
| 2019/0262139 A1 | 8/2019 | Wolters |
| 2019/0274841 A1 | 9/2019 | Hawkes et al. |
| 2019/0298542 A1 | 10/2019 | Kloss |
| 2019/0307574 A1 | 10/2019 | Nyahay et al. |
| 2019/0315169 A1 | 10/2019 | Rogness et al. |
| 2019/0328546 A1 | 10/2019 | Palagi et al. |
| 2019/0336305 A1 | 11/2019 | Joly et al. |
| 2019/0343645 A1 | 11/2019 | Miccio et al. |
| 2019/0358058 A1 | 11/2019 | Trieu |
| 2019/0388238 A1 | 12/2019 | Lechmann et al. |
| 2020/0000603 A1 | 1/2020 | McJunkin |
| 2020/0036011 A1 | 1/2020 | Numata et al. |
| 2020/0038197 A1 | 2/2020 | Morris et al. |
| 2020/0038198 A1 | 2/2020 | Miccio |
| 2020/0086625 A1 | 3/2020 | O'Neill et al. |
| 2020/0113707 A1 | 4/2020 | Petersheim et al. |
| 2020/0113709 A1 | 4/2020 | Hsieh |
| 2020/0121470 A1 | 4/2020 | Moore et al. |
| 2020/0138595 A1 | 5/2020 | Shoshtaev et al. |
| 2020/0146842 A1 | 5/2020 | Jasinski |
| 2020/0155326 A1 | 5/2020 | Hunt |
| 2020/0179128 A1 | 6/2020 | Stalcup et al. |
| 2020/0179133 A1 | 6/2020 | Ryan |
| 2020/0188120 A1 | 6/2020 | Hamzey et al. |
| 2020/0188129 A1 | 6/2020 | McShane, III et al. |
| 2020/0188132 A1 | 6/2020 | Ryan |
| 2020/0188133 A1 | 6/2020 | McShane, III et al. |
| 2020/0190680 A1 | 6/2020 | Numata et al. |
| 2020/0197189 A1 | 6/2020 | Mazur et al. |
| 2020/0214852 A1 | 7/2020 | Tipping et al. |
| 2020/0222201 A1 | 7/2020 | Mirda et al. |
| 2020/0229940 A1 | 7/2020 | Bishop et al. |
| 2020/0229945 A1 | 7/2020 | Levieux |
| 2020/0237526 A1 | 7/2020 | Wilson et al. |
| 2020/0246160 A1 | 8/2020 | Zappacosta et al. |
| 2020/0261243 A1 | 8/2020 | Unger et al. |
| 2020/0268523 A1 | 8/2020 | Barthold et al. |
| 2020/0276019 A1 | 9/2020 | Shetty et al. |
| 2020/0281727 A1 | 9/2020 | Dang et al. |
| 2020/0297494 A1 | 9/2020 | Hunt et al. |
| 2020/0297505 A1 | 9/2020 | McLaughlin |
| 2020/0315812 A1 | 10/2020 | Davis et al. |
| 2020/0323645 A1 | 10/2020 | Northcutt et al. |
| 2020/0337851 A1 | 10/2020 | Stampfli et al. |
| 2020/0337855 A1 | 10/2020 | Stauffer et al. |
| 2020/0337856 A1 | 10/2020 | Moore et al. |
| 2020/0345506 A1 | 11/2020 | Ryan et al. |
| 2020/0352735 A1 | 11/2020 | Afzal |
| 2020/0375757 A1 | 12/2020 | Sack |
| 2020/0375758 A1 | 12/2020 | Northcutt et al. |
| 2020/0376174 A1 | 12/2020 | Melkent et al. |
| 2021/0022882 A1 | 1/2021 | Dang et al. |
| 2021/0046211 A1 | 2/2021 | Deisinger et al. |
| 2021/0069383 A1 | 3/2021 | Yamaguchi et al. |
| 2021/0085481 A1 | 3/2021 | Cain et al. |
| 2021/0307909 A1 | 10/2021 | Hamzey et al. |
| 2022/0047398 A1 | 2/2022 | Nyahay et al. |
| 2022/0071777 A1 | 3/2022 | Cain et al. |
| 2022/0117753 A1 | 4/2022 | Rucker et al. |

FOREIGN PATENT DOCUMENTS

| | | |
|---|---|---|
| CN | 204931903 | 1/2016 |
| CN | 110179570 | 8/2021 |
| DE | 19722389 | 12/1998 |
| EP | 3064175 | 9/2016 |
| EP | 3494931 | 6/2019 |
| EP | 3517078 | 7/2019 |
| EP | 3603580 | 2/2020 |
| FR | 2815846 | 5/2002 |
| FR | 2955025 | 7/2011 |
| JP | H05261146 | 10/1993 |
| JP | H09503416 | 9/1997 |
| JP | 2001523129 | 11/2001 |

(56) References Cited

FOREIGN PATENT DOCUMENTS

| | | |
|---|---|---|
| JP | 20010523129 | 11/2001 |
| JP | 2004-510494 | 4/2004 |
| JP | 2006515194 | 5/2006 |
| JP | 2009-505686 | 2/2009 |
| JP | 2009504332 | 2/2009 |
| JP | 4313005 | 8/2009 |
| JP | 2010137069 | 6/2010 |
| JP | 201115959 | 1/2011 |
| JP | 2012-501236 | 1/2012 |
| JP | 20120501236 | 1/2012 |
| JP | 5328051 | 10/2013 |
| JP | 5455020 | 3/2014 |
| JP | 2014-151209 | 8/2014 |
| JP | 2015-502192 | 1/2015 |
| JP | 5684177 | 3/2015 |
| JP | 2015529150 | 10/2015 |
| JP | A2018-516646 | 6/2018 |
| JP | 2019034071 | 3/2019 |
| JP | 2019041886 | 3/2019 |
| JP | 2019180797 | 10/2019 |
| JP | 2019201688 | 11/2019 |
| JP | 6700135 | 5/2020 |
| JP | 2020199326 | 12/2020 |
| JP | 2021016498 | 2/2021 |
| JP | 7121085 | 8/2022 |
| WO | WO 9510248 | 4/1995 |
| WO | WO 9848738 | 11/1998 |
| WO | WO 9852498 | 11/1998 |
| WO | WO 0209625 | 2/2002 |
| WO | WO 0234168 | 5/2002 |
| WO | WO 03099160 | 12/2003 |
| WO | WO 2004084774 | 10/2004 |
| WO | WO 2005011523 | 2/2005 |
| WO | WO 2009051779 | 3/2006 |
| WO | WO 2007022194 | 2/2007 |
| WO | WO 2010028056 | 3/2010 |
| WO | WO 2010097632 | 9/2010 |
| WO | WO 2013067528 | 5/2013 |
| WO | W O2014052477 | 4/2014 |
| WO | WO 2014052477 | 4/2014 |
| WO | 2014168631 | 10/2014 |
| WO | WO 2016044739 | 3/2016 |
| WO | WO 2016176496 | 11/2016 |
| WO | WO 2017100366 | 6/2017 |

OTHER PUBLICATIONS

Office Action mailed Nov. 1, 2018 in U.S. Appl. No. 15/885,418.
Final Office Action mailed Feb. 25, 2019 in U.S. Appl. No. 15/885,418.
Office Action mailed Nov. 2, 2021 in U.S. Appl. No. 16/593,101.
International Search Report and Written Opinion mailed Aug. 19, 2016 in PCT/US2016/029865.
Office Action dated Apr. 3, 2019 in Chinese Application No. 2016800391036.
Office Action dated Jun. 28, 2019 in European Application No. 16722008.6-1132.
Extended European Search Report dated Dec. 8, 2020 in European Application No. 20191843.0-1132.
ISO/ASTM 52900.2015e Standard Terminology for Addiive Manufacturing—Genral Principles—Terminology, 2017, 2017.
Office Action dated Mar. 5, 2020 in Japanese Application No. 2017-556733.
Office Action dated Sep. 2, 2021 in Japanese Application No. 2020-156918.
Notice of Decision to Grant a Patent dated Jul. 7, 2022 in Japanese Application No. 2020-156918.
Office Action dated Sep. 2, 2021 in Japanese Application No. 2020-156917.
Notice of Decision to Grant a Patent dated Jul. 7, 2022 in Japanese Application No. 2020-156917.
Office Action mailed May 2, 2018 in U.S. Appl. No. 15/334,053.
Office Action mailed Dec. 3, 2018 in U.S. Appl. No. 15/334,053.
Office Action mailed Sep. 15, 2022 in U.S. Appl. No. 16/700,632.
Final Office Action mailed Jun. 2, 2023 in U.S. Appl. No. 16/700,632.
Notice of Allowance mailed Dec. 4, 2023 in U.S. Appl. No. 16/700,632.
International Search Report and Written Opinion dated Jan. 18, 2018 in PCT application No. PCT/US2017/058100.
"FDA Clears Camber Spine Technologies' 3D Printed SPIRA Open Matrix ALIF", Orthopedic Design & Technology, Aug. 5, 2017.
Supplemental Partial European Search Report dated May 15, 2020 in European Application No. 17866284.
Office Action dated Sep. 3, 2020 in European Application No. 17866284.
Office Action dated Mar. 23, 2022 in Chinese Application No. 2017800805197.
Office Action dated Mar. 25, 2021 in Japanese Application No. 2019-543187.
Office Action dated Aug. 5, 2021 in Japanese Application No. 2019-543187.
Office Action dated Jan. 12, 2022 in Japanese Application No. 2019-543187.
Preliminary Office Action dated Jan. 24, 2022 in Brazilian Application No. 112019008325-1.
Office Action dated Feb. 16, 2023 in Japanese Application No. 2021-197842.
Office Action dated Nov. 30, 2023 in Japanese Application No. 2021-197842. .
Office Action mailed Jul. 8, 2019 in U.S. Appl. No. 15/884,845.
Final Office Action mailed Oct. 24, 2019 in U.S. Appl. No. 15/884,845.
Office Action mailed Apr. 24, 2024 in U.S. Appl. No. 16/924,823.
International Search Report and Written Opinion dated Apr. 26, 2019 in PCT application No. PCT/US19/15946.
Office Action dated Dec. 9, 2021 in Japanese Application No. 2020-540800.
Office Action mailed Apr. 27, 2023 in Japanese Application No. 2022-086976.
Notice of Allowance dated Jan. 18, 2024 ir Japanese Application No. 2022-086976.
Office Action dated Nov. 5, 2020 in Australian Application No. 2019214987.
Office Action dated Oct. 15, 2021 in Australian Application No. 2019214987.
Office Action dated Mar. 27, 2023 in Australian Application No. 2022200666.
Office Action mailed Oct. 25, 2018 in U.S. Appl. No. 15/791,279.
Final Office Action mailed Mar. 1, 2019 in U.S. Appl. No. 15/791,279.
Office Action mailed Mar. 1, 2022 in U.S. Appl. No. 16/659,011.
Final Office Action mailed Jun. 21, 2022 in U.S. Appl. No. 16/659,011.
Office Action mailed Feb. 27, 2023 in U.S. Appl. No. 16/659,011.
Office Action mailed Apr. 20, 2023 in JP Application No. 2022-124717.
Office Action mailed Jan. 18, 2024 in JP Application No. 2022-124717.

* cited by examiner

IMPLANT WITH IMPROVED BONE CONTACT

CROSS-REFERENCE TO RELATED APPLICATIONS

This application is a continuation of Sack, U.S. patent application Ser. No. 16/995,192, filed Aug. 17, 2020, and titled "Implant with Improved Bone Contact," which is a continuation of Sack, U.S. Pat. No. 10,744,001, issued Aug. 18, 2020, and titled "Implant with Improved Bone Contact." The entire disclosure of each application listed above is incorporated herein by reference.

BACKGROUND

The embodiments are generally directed to implants for supporting bone growth in a patient.

A variety of different implants are used in the body. Implants used in the body to stabilize an area and promote bone ingrowth provide both stability (i.e., minimal deformation under pressure over time) and space for bone ingrowth.

Spinal fusion, also known as spondylodesis or spondylosyndesis, is a surgical treatment method used for the treatment of various morbidities such as degenerative disc disease, spondylolisthesis (slippage of a vertebra), spinal stenosis, scoliosis, fracture, infection, or tumor. The aim of the spinal fusion procedure is to reduce instability and thus pain.

In preparation for the spinal fusion, most of the intervertebral disc is removed. An implant, the spinal fusion cage, may be placed between the vertebra to maintain spine alignment and disc height. The fusion, i.e., bone bridge, occurs between the endplates of the vertebrae.

SUMMARY

In one aspect, an intervertebral implant includes a body formed as an open lattice structure. The body includes a central core and an outer portion. The body also includes a contact surface and a perimeter surface. The contact surface is configured to confront a bone plate, the contact surface being spaced from the central core of the body. The contact surface can include a node, the node being an intersection of a first strut and a second strut. The first strut has a first longitudinal length and a first lateral width, the first longitudinal length being longer than the first lateral width. The second strut has a second longitudinal length and a second lateral width, the second longitudinal length being longer than the second lateral width. The node can include an enlarged contact member that extends between the first lateral width and the second lateral width.

In another aspect, an intervertebral implant includes a body formed as a lattice structure. The body includes a central core and an outer portion. The body also includes a superior surface, an inferior surface and a perimeter surface. The superior surface is configured to confront an upper bone plate. The superior surface is spaced from the central core of the body. The inferior surface is configured to confront a lower bone plate. The inferior surface is spaced from the central core of the body. The superior surface includes a node, the node being an intersection of a first strut and a second strut. The first strut has a first longitudinal length and a first lateral width, the first longitudinal length being longer than the first lateral width. The second strut has a second longitudinal length and a second lateral width, the second longitudinal length being longer than the second lateral width. The node can include an enlarged contact member that extends beyond the first lateral width and the second lateral width.

In another aspect, a method of making an intervertebral implant having a body is provided. The body includes a central core and an outer portion. The outer portion includes a superior surface, an inferior surface, and a perimeter surface. The method includes the step of additively manufacturing a first layer. The first layer is proximate a base plate. The first layer forms a part of the perimeter surface. The method also includes a step of continuing to additively manufacture the perimeter surface. The method also includes a step of additively manufacturing the superior surface and the inferior surface, wherein the superior surface extends away from the base plate, and wherein the inferior surface extends away from the base plate.

Other systems, methods, features, and advantages of the embodiments will be, or will become, apparent to one of ordinary skill in the art upon examination of the following figures and detailed description. It is intended that all such additional systems, methods, features, and advantages be included within this description and this summary, be within the scope of the embodiments, and be protected by the following claims.

BRIEF DESCRIPTION OF THE DRAWINGS

The embodiments can be better understood with reference to the following drawings and description. The components in the figures are not necessarily to scale, emphasis instead being placed upon illustrating the principles of the embodiments. Moreover, in the figures, like reference numerals designate corresponding parts throughout the different views.

DETAILED DESCRIPTION

Any of the embodiments described herein may make use of any of the body/support structures, frames, plates, coils, or other structures disclosed in:

Hunt, U.S. Pat. No. 8,430,930, issued Apr. 30, 2013 and entitled "Truss Implant";

Hunt, U.S. Patent Appl. Publ. No. 2011/0313532, published Dec. 22, 2011 and entitled "Bone Implant Interface System and Method";

Hunt, U.S. Patent Appl. Publ. No. 2013/0030529, published Jan. 31, 2013 and entitled "Implant Interface system and method";

Hunt et al., U.S. Patent Appl. Publ. No. 2013/0123935, published May 16, 2013 and entitled "Method of Length Preservation During Bone Repair";

Hunt, U.S. Patent Appl. Publ. No. 2013/0218282, published Aug. 22, 2013 and entitled "Prosthetic Implant for Ball and Socket Joints and Method of Use";

Hunt et al., U.S. Pat. No. 9,271,845, issued Mar. 1, 2016 and entitled "Programmable Implants and Methods of Using Programmable Implants to Repair Bone Structures";

Hunt, U.S. Pat. No. 9,636,226, issued May 2, 2017 and entitled "Traumatic Bone Fracture Repair Systems and Methods";

Hunt, U.S. Patent Appl. Publ. No. 2014/0288650, published Sep. 25, 2014 and entitled "Motion Preservation Implant and Methods"; and Sack, U.S. Patent Appl. Publ. No. 2019/0151113, published May 23, 2019, and entitled "Implant with Improved Flow Characteristics."

The entire disclosures of the patents and publications listed above are incorporated herein by reference in their entirety.

Implantation

Figure 1:
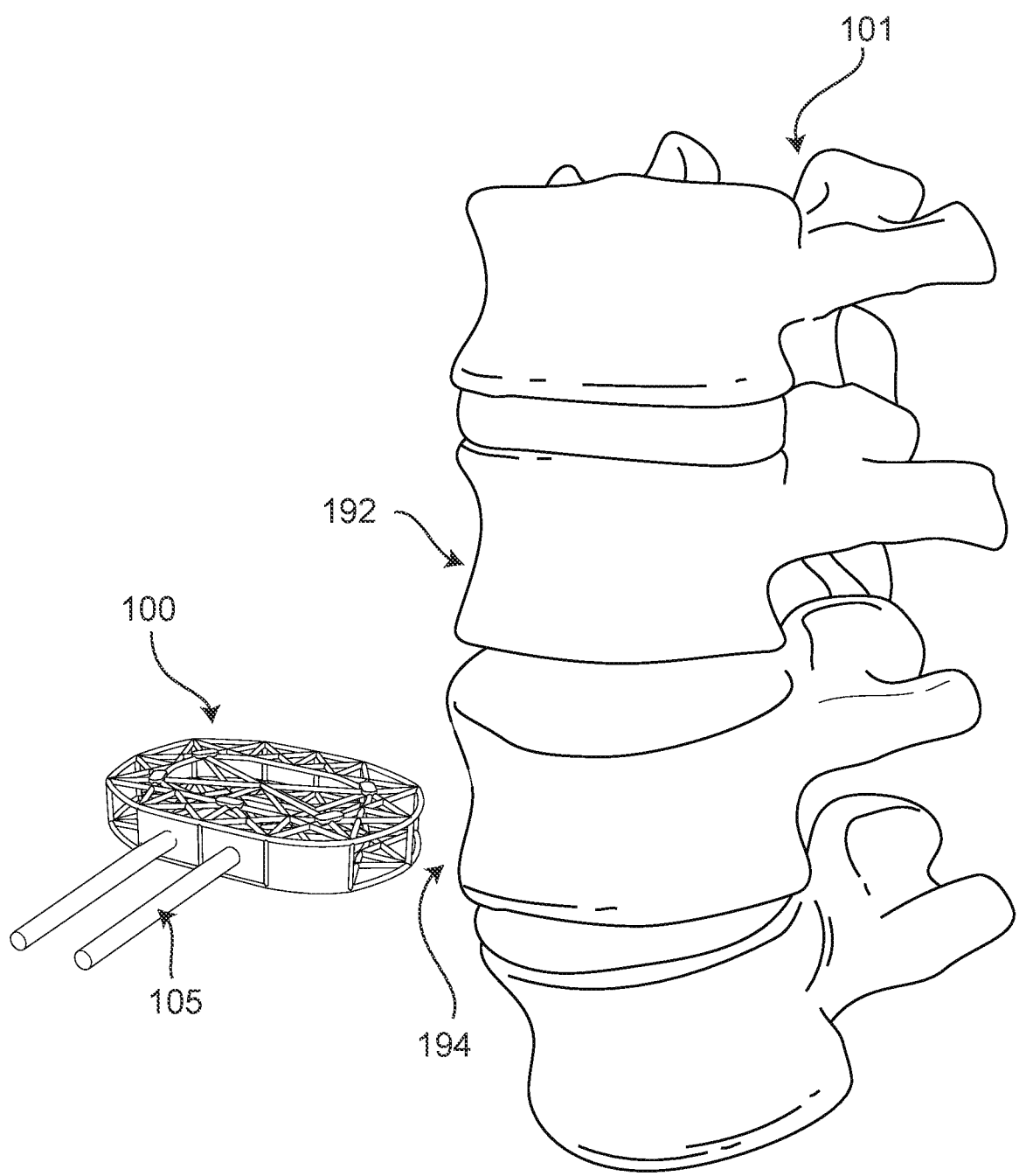
FIG. 1 is a schematic isometric view of a step of implanting a device into a spinal column, according to an embodiment.
Figure 2:
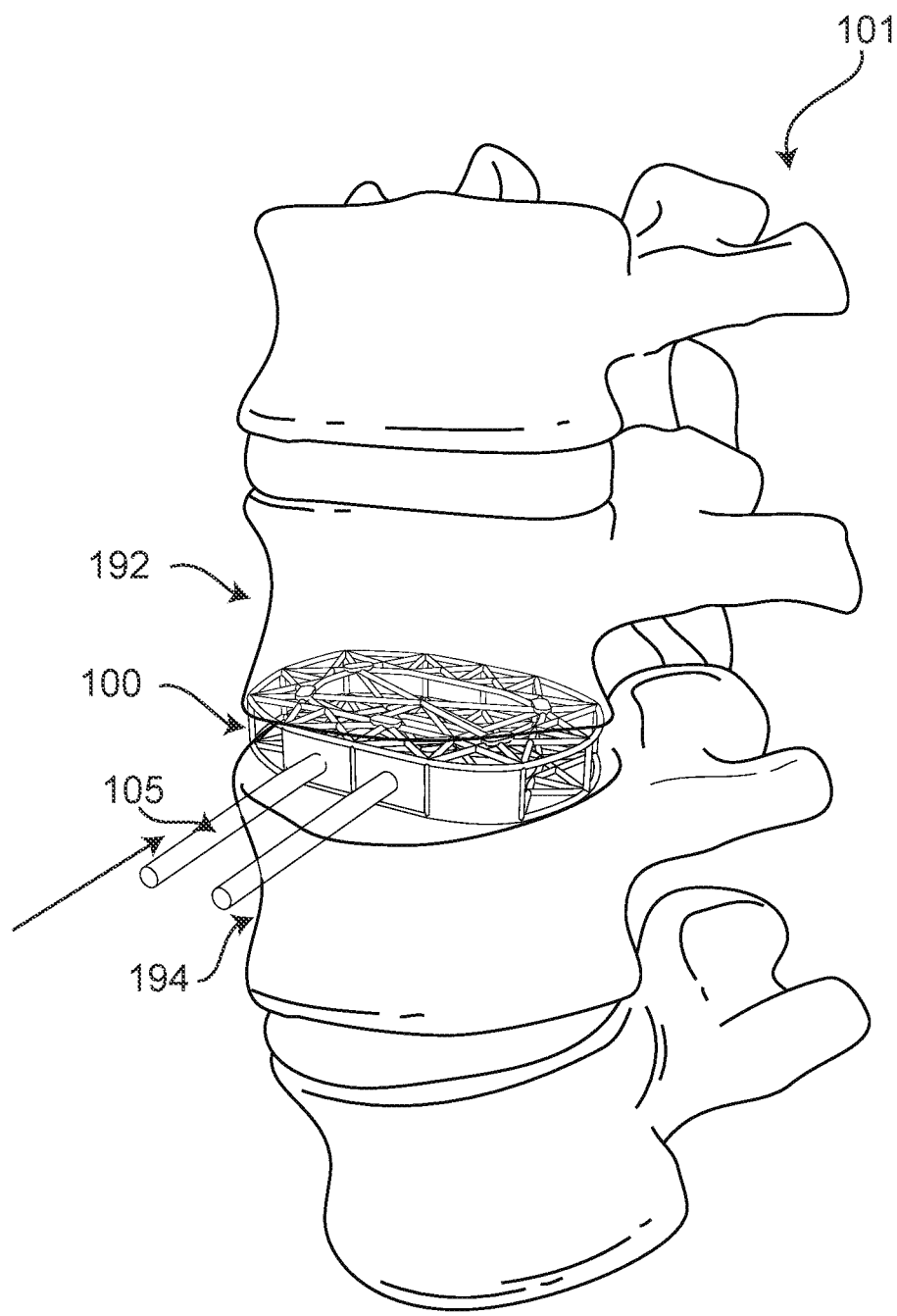
FIG. 2 is a schematic isometric view of a device implanted within a spinal column, according to an embodiment.

FIG. 1 is a schematic view of an embodiment of an implant 100. For purposes of context, implant 100 is shown adjacent to a portion of a spinal column 101. In FIG. 2, an embodiment of implant 100 is shown following insertion between two adjacent vertebrae (vertebra 192 and vertebra 194) within spinal column 101. This insertion is facilitated by use of an insertion tool 105, which is shown schematically in FIGS. 1 and 2.

For purposes of this disclosure, implant 100 may also be referred to as a cage or fusion device. In some embodiments, implant 100 is configured to be implanted within a portion of the human body. In some embodiments, implant 100 may be configured for implantation into the spine. In some embodiments, implant 100 may be a spinal fusion implant, or spinal fusion device, which is inserted between adjacent vertebrae to provide support and/or facilitate fusion between the vertebrae.

In some embodiments, implant 100 may be inserted using an anterior lumbar interbody fusion (ALIF) surgical procedure, where the disc space is fused by approaching the spine through the abdomen. In the ALIF approach, a three-inch to five-inch incision is typically made near the abdomen and the abdominal muscles are retracted to the side. In some cases, implant 100 can be inserted through a small incision in the front or anterior side of the body. In some cases, an anterior approach may afford improved exposure to the disc space to a surgeon. The anterior approach can allow a larger device to be used for the fusion, increasing the surface area for fusion to occur and allowing for more postoperative stability. An anterior approach often makes it possible to reduce some of the deformity caused by various conditions, such as isthmic spondylolisthesis. Insertion and placement of the disc along the front of a human body can also re-establish the patient's normal sagittal alignment in some cases, giving individuals a more normal inward curve to their low back.

Introduction to Implant

For purposes of clarity, reference is made to various directional adjectives throughout the detailed description and in the claims. As used herein, the term "anterior" refers to a side or portion of an implant that is intended to be oriented toward the front of the human body when the implant has been placed in the body. Likewise, the term "posterior" refers to a side or portion of an implant that is intended to be oriented toward the back of the human body following implantation. In addition, the term "superior" refers to a side or portion of an implant that is intended to be oriented toward a top (e.g., the head) of the body while "inferior" refers to a side or portion of an implant that is intended to be oriented toward a bottom of the body. Reference is also made herein to "lateral" sides or portions of an implant, which are sides or portions facing along lateral directions of the body following implantation.

Figure 3:
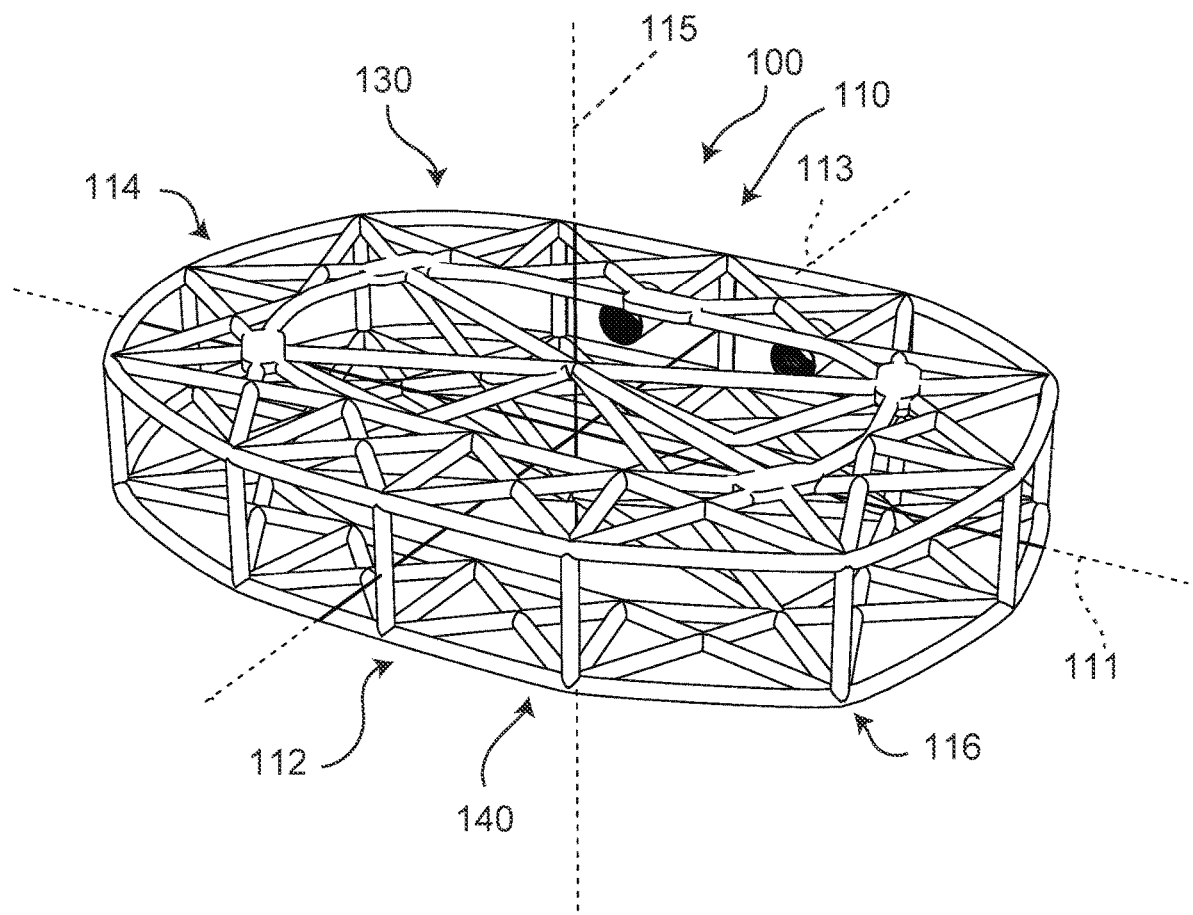
FIG. 3 is a schematic isometric view of an embodiment of an implant.
Figure 4:
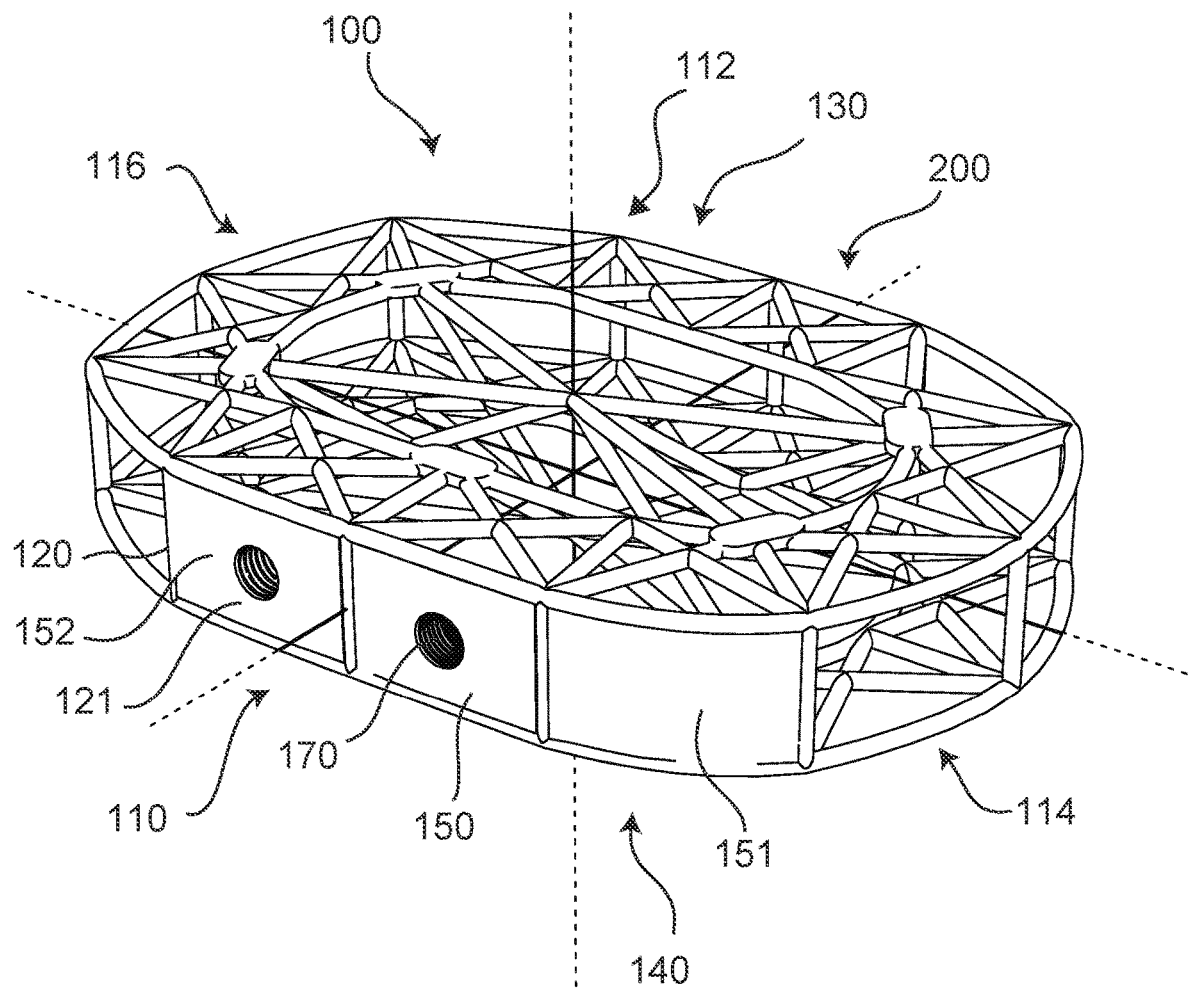
FIG. 4 is a schematic isometric view of an embodiment of an implant.

FIGS. 3-4 illustrate isometric views of an embodiment of implant 100. Specifically, FIG. 3 is a posterior isometric view while FIG. 4 is an anterior isometric view. In FIGS. 3-4, implant 100 is understood to be configured with an anterior side 110 and a posterior side 112. Implant 100 may also include a first lateral side 114 and a second lateral side 116 that extend between posterior side 112 and anterior side 110 on opposing sides of implant 100. Furthermore, implant 100 may also include a superior side 130 and an inferior side 140.

Implant 100 may also be associated with various edges that are located at the intersections between various sides. For example, superior side 130 and first lateral side 114 may meet at a superior-lateral edge. Likewise, inferior side 140 and first lateral side 114 may meet at an inferior-lateral edge. It may be appreciated that the term "edge" as used herein is not limited to a precise contour of implant 100 and is used instead to refer to a general region proximate the intersection of two sides or faces of implant 100.

Reference is also made to directions or axes that are relative to the implant itself, rather than to its intended orientation with regards to the body. For example, the term "central" refers to a part that is located closer to the center of the implant. As used herein, the "center of the implant" is generally defined as a vertical axis extending through the approximate middle of the implant, which may be approximately the location of the center of mass or the dimensional middle (i.e., equidistant from opposing sides.

An implant may also be associated with various axes. Referring to FIG. 3, implant 100 may be associated with a lateral axis 111 that extends along implant 100 between first lateral side 114 and second lateral side 116. Additionally, implant 100 may be associated with a posterior-anterior axis 113 that extends between posterior side 112 and anterior side 110. Moreover, implant 100 may be associated with a vertical axis 115 (which may also be referred to as a superior-inferior axis) that extends along the thickness dimension of implant 100 and which is generally perpendicular to both lateral axis 111 and posterior-anterior axis 113.

An implant may also be associated with various reference planes or surfaces. As used herein, the term "median plane" refers to a vertical plane that passes from the anterior side to the posterior side of the implant, dividing the implant into right and left halves, or lateral halves. As used herein, the term "transverse plane" refers to a horizontal plane located in the center of the implant that divides the implant into superior and inferior halves. As used herein, the term "coronal plane" refers to a vertical plane located in the center of the implant that divides the implant into anterior and posterior halves. In some embodiments, the implant is symmetric about two planes, such as the transverse plane.

Implant 100 is comprised of one or more body members attached to one or more bone contacting elements. In the embodiments shown in FIGS. 3-4, implant 100 includes a first body member 120. First body member 120 generally comprises a block-like member forming a solid end or side for implant 100. In the exemplary embodiment, first body member 120 is disposed at an anterior end of implant 100. Alternatively, in other embodiments, implant 100 could comprise one or more body members on either of the lateral sides or on the posterior side of implant 100.

In different embodiments, the geometry of one or more body members could vary. In some embodiments, first body member 120 may comprise a solid structure including various connected faces. As seen in FIG. 4, first body member 120 includes exterior surface 121 that is further comprised of a first central face 150, an angled face 151, and a second central face 152.

Some embodiments can include one or more fastener-receiving provisions. In some embodiments, an implant can include one or more threaded cavities. In some embodiments, a threaded cavity can be configured to mate with a corresponding threaded tip on an implantation tool or device. In other embodiments, a threaded cavity can receive a fastener for purposes of fastening an implant to another device or component in an implantation system that uses multiple implants and/or multiple components.

As best seen in FIG. 4, implant 100 includes a threaded cavity 170 disposed in first body member 120. In some embodiments, threaded cavity 170 may receive the threaded tip of an implantation tool (not shown). Such a tool could be used to drive implant 100 between adjacent vertebral bodies.

In some embodiments, one or more bone contacting elements may extend from first body member 120. In the embodiment shown in FIGS. 3-4, implant 100 includes a plurality of bone contacting elements 200 that may be attached, and/or continuously formed (or "integrally formed") with, first body member 120.

As used herein, each bone contacting element comprises a distinctive member or element that spans a region or area of an implant. In some embodiments, these elements may overlap or intersect, similar to elements in a lattice or other 3D mesh structure. In other embodiments, the elements may not overlap or intersect. Some embodiments may use elongated elements, in which the length of the element is greater than its width and its thickness. For example, in embodiments where an element has an approximately circular cross-sectional shape, the element has a length greater than its diameter. In the embodiments seen in FIGS. 3-4, each bone contacting element is seen to have an approximately rounded or circular cross-sectional shape (i.e., the element has the geometry of a solid tube) along at least a portion of the element. However, in other embodiments, an element could have any other cross-sectional shape, including, but not limited to, various polygonal cross-sectional shapes (e.g., triangular, rectangular, etc.), as well as any other regular and/or irregular cross-sectional shapes. Examples of embodiments including a bone contacting element with a flattened cross-sectional shape are shown in FIGS. 13-16 and discussed in further detail below. In some cases, for example, the cross-sectional shape of a bone contacting element could vary along its length (e.g., the diameter could change along its length).

Geometry of Bone Contacting Elements

Embodiments can include provisions for protecting bone growth along and adjacent to bone contacting elements of an implant. In some embodiments, a bone contacting element can be configured with a geometry that helps to protect new bone growth in selected regions that may be referred to as "protected fusion zones." In a protected fusion zone, new bone growth may be partially protected from forces transmitted directly between vertebrae and bone contacting surfaces of an implant, thereby increasing the rate at which new bone growth may propagate through the implant.

In some embodiments, a bone contacting element can have a spiral, helical, or twisted geometry that provide a series of such protected fusion zones for enhanced bone growth. In other embodiments, a bone contacting element can have a planar undulating geometry (e.g., sinusoidal) that may also create protected fusion zones. In some embodiments, an implant may include bone contacting elements with a helical geometry and other bone contacting elements with a sinusoidal, or planar undulating geometry.

Some bone contacting elements may have a generalized helical geometry. As used herein, a "generalized helical geometry" or "spiraling geometry" refers to a geometry where a part (portion, member, etc.) winds, turns, twists, rotates, or is otherwise curved around a fixed path. In some cases, the fixed path could be straight. In other cases, the fixed path can be curved. In the present embodiments, for example, the fixed path is generally a combination of straight segments and curved segments.

Curves having a generalized helical geometry (also referred to as generalized helical curves) may be characterized by "coils," "turns," or "windings" about a fixed path. Exemplary parameters that may characterize the specific geometry of a generalized helical curve can include coil diameter (including both a major and minor diameter) and the pitch (i.e., spacing between adjacent coils). In some cases, the "amplitude" of a coil or loop may also be used to describe the diameter or widthwise dimension of the coil or loop. Each of these parameters could be constant or could vary over the length of a generalized helical curve.

Generalized helical curves need not be circular or even round. In some embodiments, for example, a generalized helical curve could have a linearly segmented shape (or locally polygonal shape) such that each "coil" or "turn" is comprised of straight line segments rather than arcs or other curved segments. Generalized helical curves may also include combinations of curved and straight segments.

For purposes of characterizing the geometry of one or more bone contacting elements, each bone contacting element can be identified with one or more curves. Each bone contacting element may be identified with a central curve. The central curve of each bone contacting element may be defined as a curve that extends along the length (or longest dimension) of the bone contacting element such that each point along the curve is centrally positioned within the bone contacting element. In addition, each bone contacting element may be identified with one or more exterior surface curves. An exterior surface curve of a bone contacting element may be defined as a curve that extends along the length (or longest dimension) of the bone contacting element such that each point along the curve is positioned on the exterior surface.

In some situations, the approximately rounded or circular cross-sectional shape of bone contacting elements may apply unwanted stress to bone in areas where the bone contacting elements of the implant are in direct contact with the bone. For example, particularly in the case of older patients and/or patients with osteoporosis or other conditions that result in brittle or fragile bones, the stress associated with the direct contact from the approximately rounded or circular cross-sectional shape of bone contacting elements of the implant can weaken or otherwise damage the bone in the proximity of the implant. Accordingly, in some embodiments, an implant may be provided with components that are configured for improved bone contact.

Figure 5:
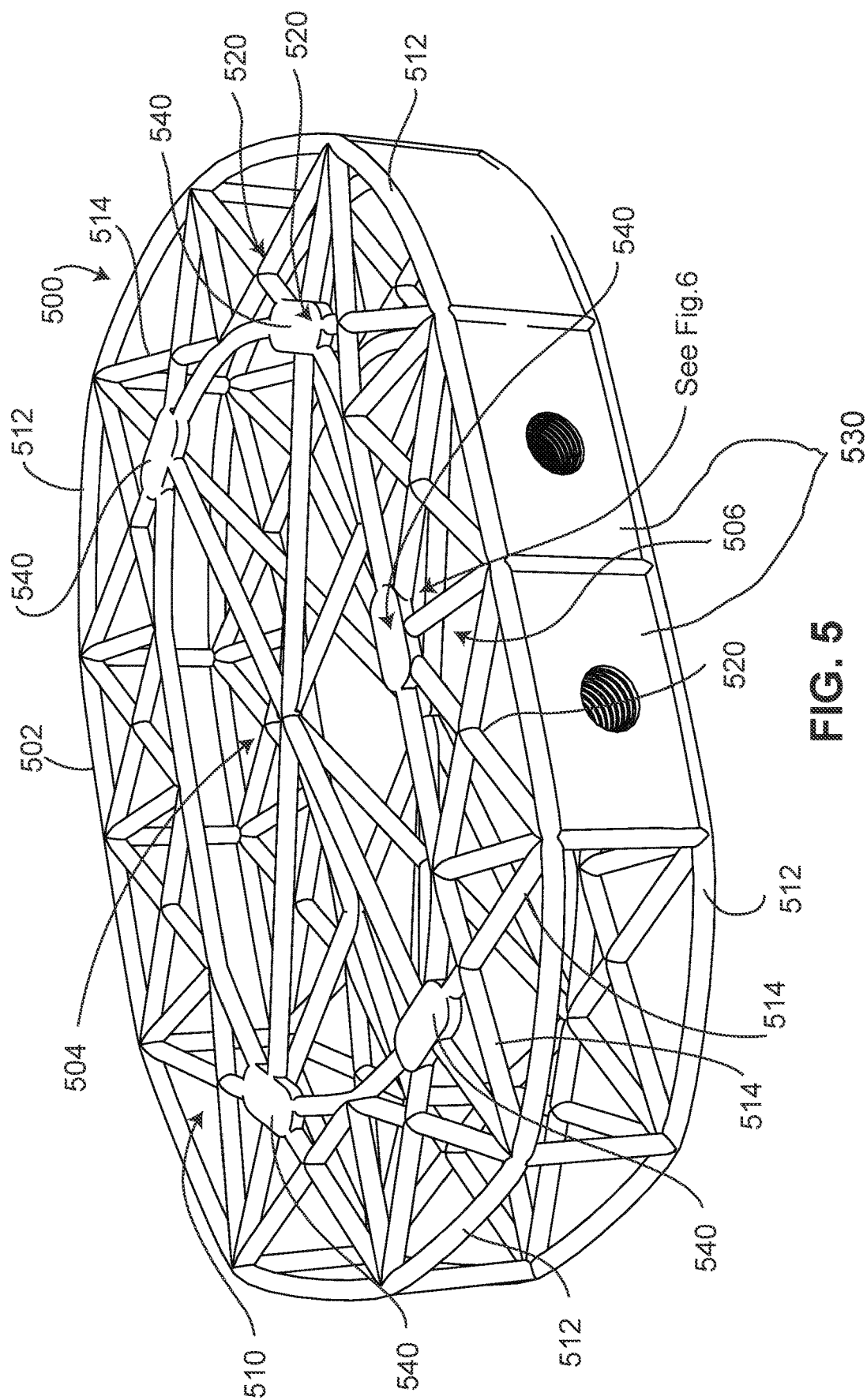
FIG. 5 is a schematic isometric view of an embodiment of an implant configured for improved bone contact.

FIG. 5 is a schematic view of an exemplary embodiment of an implant 500 configured for improved bone contact. In this embodiment, implant 500 includes a body 502 formed as an open lattice structure made of a plurality of bone contacting elements or struts 510. Body 502 can include a central core 504 and an outer portion 506. Central core 504 is disposed approximately within the middle or center of body 502 of implant 500. Outer portion 506 is disposed outward from central core 504 and generally surrounds central core 504. Outer portion 506 extends from central core 504 to the perimeter edge of implant 500.

Plurality of struts 510 form the open lattice structure of body 502 of implant 500. Plurality of struts 510 are generally elongate members having a longitudinal length and a lateral width, with the longitudinal length being longer than the lateral width. Plurality of struts 510 can include one or more outer struts 512 and one or more inner struts 514. In this embodiment, outer struts 512 are disposed along the perimeter edge of implant 500 and define the boundary of outer portion 506. Outer struts 512 can include substantially straight segments and/or curved or arched segments. In some embodiments, outer struts 512 may include combinations of curved and straight segments that assist with providing and defining the overall shape of implant 500.

Inner struts 514 extend from the perimeter edge of implant 500 defined by outer struts 512 inward toward central core 504 of body 502. Inner struts 514 intersect with one another at one or more nodes 520. A plurality of inner struts 514 intersects at a plurality of nodes 520 to collectively form the open lattice structure of body 502. In this embodiment, inner struts 514 are substantially straight segments. In other embodiments, inner struts 514 can include substantially straight segments, curved or arched segments, and/or a combination of curved and straight segments to form an open lattice structure.

Body 502 of implant 500 further includes a contact surface and a perimeter surface. The contact surface is configured to confront a bone plate when implant 500 is implanted into a patient. In this embodiment, the contact surface is spaced apart from central core 504 of body 502. In various embodiments, the contact surface can be a superior surface configured to confront an upper bone plate and/or an inferior surface configured to confront a lower bone plate. In some embodiments, an implant may include a superior contact surface, an inferior contact surface, or both.

The perimeter surface of body 502 of implant 500 is disposed approximately orthogonal to the contact surface or contact surfaces of implant 500 and extends substantially circumferentially around the perimeter edge of outer portion 506 of implant 500. Generally, the perimeter surface of body 502 is not configured to confront a bone plate when implant 500 is implanted into a patient.

In some embodiments, outer portion 506 of body 502 can include one or more screw plates 530. Screw plates 530 may include components configured to assist insertion and placement of implant 500 within a patient. In this embodiment, the outer surface of screw plates 530 is substantially planar with the remaining perimeter surface of body 502. In other embodiments, portions of screw plates 530 can extend beyond the perimeter surface of body 502 of implant 500.

In some embodiments, the contact surface of an implant can include components configured for improved bone contact. In an exemplary embodiment, superior and/or inferior contact surfaces of body 502 of implant 500 include one or more enlarged contact members 540. Enlarged contact members 540 can be disposed at various locations on the contact surfaces of body 502 of implant 500. In this embodiment, enlarged contact members 540 are located at one or more of plurality of nodes 520 where two or more of plurality of struts 510 intersect with each other. Additional enlarged contact members 540 can be disposed at other nodes of intersection between two or more of plurality of struts 510, including outer struts 512, inner struts 514, and/or a combination of both across various portions of the contact surfaces of implant 500.

Figure 6:
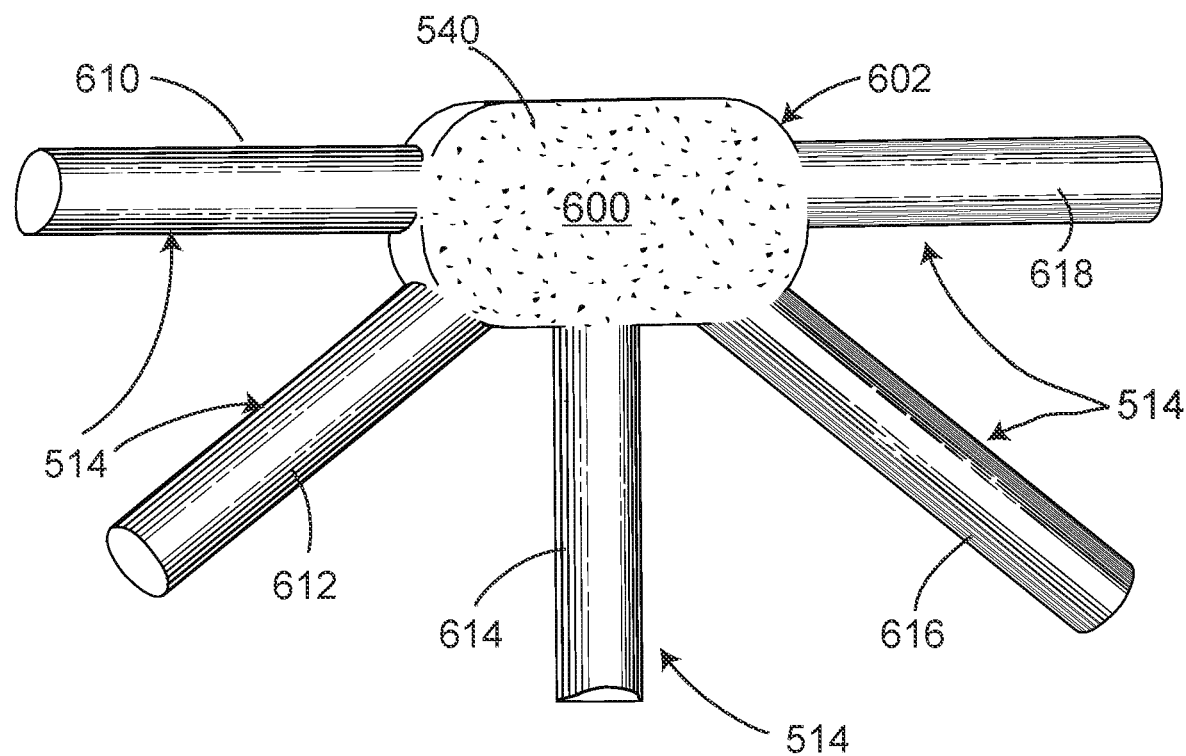
FIG. 6 is an enlarged top view of the implant of FIG. 5, in which a single enlarged contact member is shown.

FIG. 6 illustrates an enlarged view of an exemplary embodiment of an enlarged contact member 540. In an exemplary embodiment, enlarged contact member 540 is disposed at the node of an intersection between two or more of plurality of struts 510. In this embodiment, enlarged contact member 540 is disposed at the node of an intersection between five inner struts 514, including a first strut 610, a second strut 612, a third strut 614, a fourth strut 616, and a fifth strut 618. Enlarged contact member 540 includes a substantially flattened surface 600 that is configured to confront a bone plate of a patient. In some cases, flattened surface 600 of enlarged contact member 540 can be textured to assist with adhesion to the bone plate.

In an exemplary embodiment, enlarged contact member 540 has a generally ovoid or rounded shape defined by an outer perimeter edge 602. In this embodiment, outer perimeter edge 602 extends beyond the node of intersection between first strut 610, second strut 612, third strut 614, fourth strut 616, and fifth strut 618. In addition, enlarged contact member 540 also extends beyond the lateral width of each of first strut 610, second strut 612, third strut 614, fourth strut 616, and fifth strut 618. That is, enlarged contact member 540 is wider than each of the lateral widths of first strut 610, second strut 612, third strut 614, fourth strut 616, and fifth strut 618. Flattened surface 600 of enlarged contact member 540 provides a substantially greater surface area for confronting a bone plate than would be provided by the node of intersection of plurality of struts 510 and/or the lateral width of any of the individual struts themselves. With this arrangement, enlarged contact member 540 assists with providing improved bone contact to implant 500 and allows forces and/or stresses applied to the bone to be distributed across the larger surface area of flattened surface 600.

Figure 7:
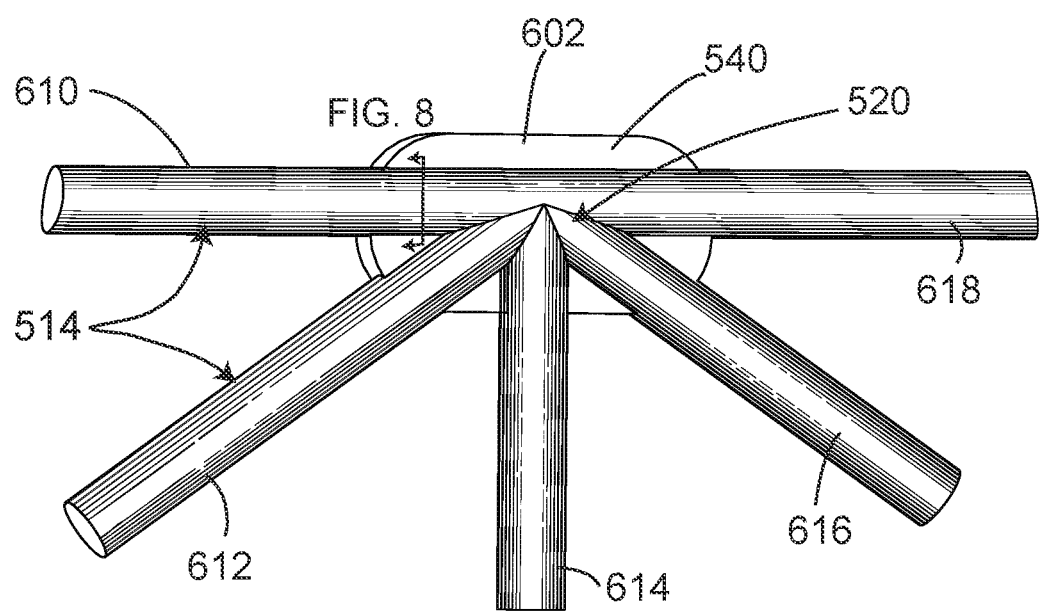
FIG. 7 is a schematic bottom view of the enlarged contact member shown in FIG. 6.

Referring now to FIG. 7, the underside or bottom view of enlarged contact member 540 shown in FIG. 6 is illustrated. In this embodiment, plurality of struts 510, in this case, plurality of inner struts 514, including first strut 610, second strut 612, third strut 614, fourth strut 616, and fifth strut 618, intersect at node 520. Enlarged contact member 540 extends over node 520 such that outer perimeter edge 602 is spaced outward from node 520. As can be seen in FIG. 7, enlarged contact member 540 also extends beyond the lateral width of each of first strut 610, second strut 612, third strut 614, fourth strut 616, and fifth strut 618.

In this embodiment, on the underside of enlarged contact member 540, first strut 610, second strut 612, third strut 614, fourth strut 616, and fifth strut 618 have a substantially rounded cross-sectional shape. As noted above, on the opposite side of enlarged contact member 540, flattened surface 600 is substantially flat and is configured to confront a bone plate of a patient.

Figure 8:
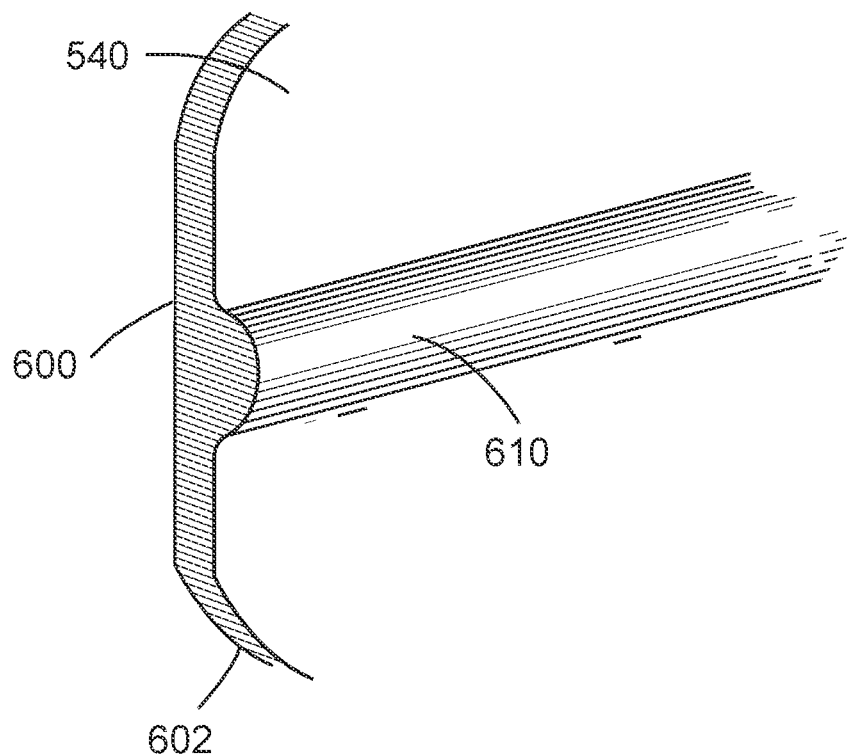
FIG. 8 is a cross-section view of the enlarged contact member shown in FIG. 7.

FIG. 8 illustrates a cross section of a portion of enlarged contact member 540 taken along the line shown in FIG. 7. The cross-sectional view of the portion of enlarged contact member 540 shows substantially flattened surface 600 on one side of enlarged contact member 540 and the substantially rounded cross-sectional shape of first strut 610 on the opposite side. In this embodiment, substantially flattened surface 600 is oriented on implant 500 to face outward from central core 504 of implant. With this arrangement, one or more flattened surfaces 600 of a plurality of enlarged contact members 540 can be configured to provide superior and/or inferior contact surfaces of body 502 of implant 500.

In one embodiment, the shape of enlarged contact member 540 may be asymmetrical with respect to the intersection of two or more struts of plurality of struts 510. That is, a portion of enlarged contact member 540 that extends in one direction from a node of intersection between two or more struts of plurality of struts 510 may have a different shape and/or size than another portion of enlarged contact member 540 that extends in a different direction from the node of intersection. For example, FIGS. 9 and 10, described in more detail below, illustrate two alternate embodiments of an enlarged contact member having a generally asymmetrical shape with respect to the intersection of two or more struts of a plurality of struts.

Figure 9:
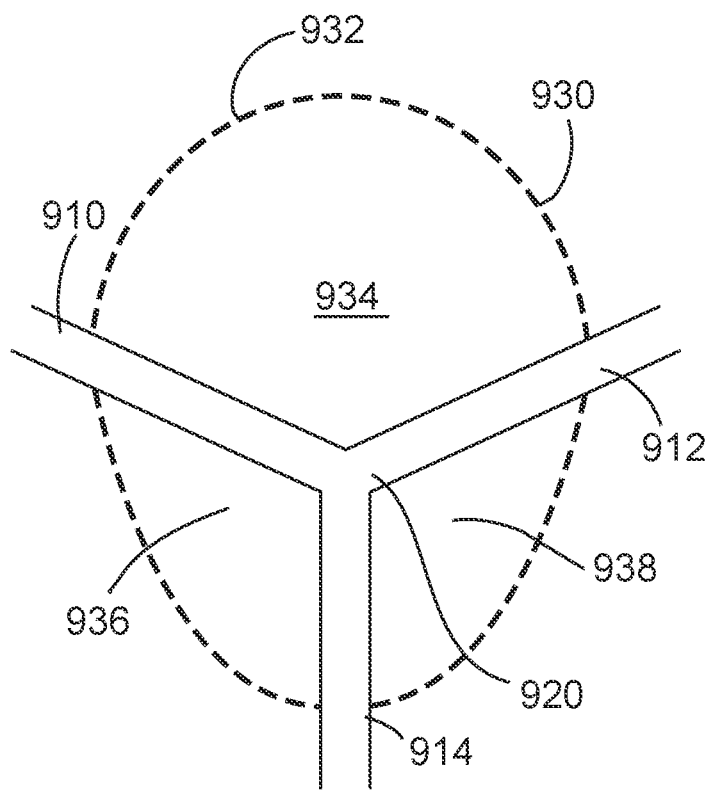
FIG. 9 is a schematic view of an alternate embodiment of an enlarged contact member for an implant.

Referring now to FIG. 9, an underside bottom view of an alternate embodiment of an asymmetric enlarged contact member 930 is illustrated. In this embodiment, a plurality of struts, including a first strut 910, a second strut 912, and a third strut 914, intersect at a node 920. Asymmetric enlarged contact member 930 extends over node 920 such that an outer perimeter edge 932 of asymmetric enlarged contact member 930 is spaced outward from node 920. Asymmetric enlarged contact member 930 also extends over the lateral width of portions of each of first strut 910, second strut 912, and third strut 914. In this embodiment, the shape of asymmetric enlarged contact member 930 is asymmetric with respect to the intersection of at least two struts of first strut 910, second strut 912, and/or third strut 914.

For example, as shown in FIG. 9, asymmetric enlarged contact member 930 includes three areas disposed between the intersection of adjacent struts, including a first area 934 disposed between the intersection of first strut 910 and second strut 912, a second area 936 disposed between the intersection of first strut 910 and third strut 914, and a third area 938 disposed between the intersection of second strut 912 and third strut 914. In this example, first area 934 is larger than either or both of second area 936 and third area 938.

Asymmetric enlarged contact member 930 is asymmetrically disposed with respect to the intersection of at least two struts of first strut 910, second strut 912, and/or third strut 914 such that first area 934 is asymmetric with second area 936 and third area 938 with respect to the intersection of first strut 910 and second strut 912, second area 936 is asymmetric with first area 934 and third area 938 with respect to the intersection of second strut 912 and third strut 914, and third area 938 is asymmetric with first area 934 and second area 936 with respect to the intersection of first strut 910 and third strut 914. With this arrangement, asymmetric enlarged contact member 930 may provide a larger surface area for a contact surface of an implant in a particular location on the implant.

In an exemplary embodiment, asymmetric enlarged contact member 930 may have an approximately teardrop or pear shape. The teardrop or pear shape of asymmetric enlarged contact member 930 shown in FIG. 9 has a wider width at one end and a narrower width at the opposite end. For example, asymmetric enlarged contact member 930 is wider at one end located in first area 934 and is narrower at the opposite end located in second area 936 and/or third area 938. With this configuration, outer perimeter edge 932 of asymmetric enlarged contact member 930 defines a teardrop or pear shape.

Figure 10:
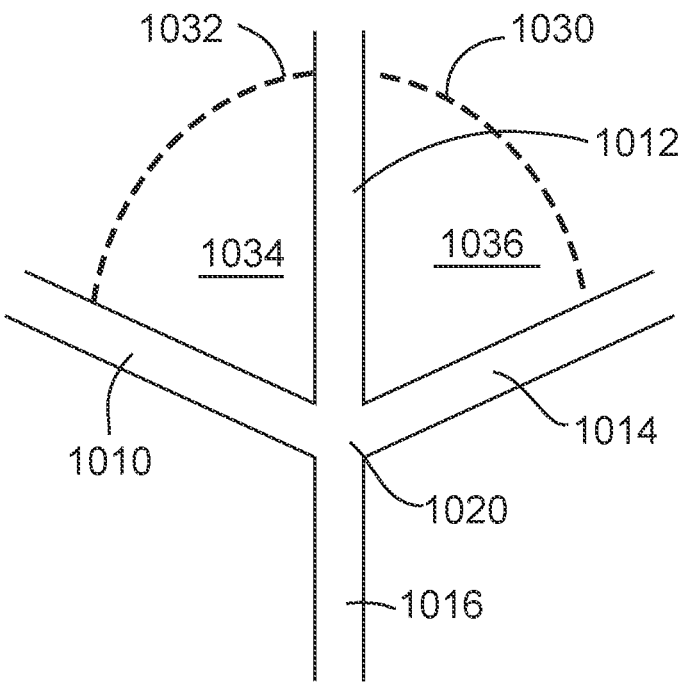
FIG. 10 is a schematic view of another alternate embodiment of an enlarged contact member for an implant.

Referring now to FIG. 10, another alternate embodiment of an asymmetric enlarged contact member 1030 is illustrated from a bottom view. In this embodiment, a plurality of struts, including a first strut 1010, a second strut 1012, a third strut 1014, and a fourth strut 1016 intersect at a node 1020. Asymmetric enlarged contact member 1030 extends away from node 1020 such that an outer perimeter edge 1032 of asymmetric enlarged contact member 1030 is spaced outward from node 1020. Asymmetric enlarged contact member 1030 also extends over the lateral width of portions of first strut 1010, second strut 1012, and third strut 1014. In this embodiment, asymmetric enlarged contact member 1030 does not extend in the opposite direction over node 1020 and does not extend over any portion of the lateral width of fourth strut 1016. In this embodiment, the shape of asymmetric enlarged contact member 930 is asymmetric with respect to the intersection of at least two struts of first strut 1010, second strut 1012, and/or third strut 1014.

For example, as shown in FIG. 10, asymmetric enlarged contact member 1030 includes two areas disposed between the intersection of adjacent struts, including a first area 1034 disposed between the intersection of first strut 1010 and second strut 1012 and a second area 1036 disposed between the intersection of second strut 1012 and third strut 1014. In contrast with the embodiment of FIG. 9, in this embodiment, asymmetric enlarged contact member 1030 is absent between the intersection between third strut 1014 and fourth strut 1016. In this embodiment, asymmetric enlarged contact member 1030 also is absent between the intersection between first strut 1010 and fourth strut 1016.

Asymmetric enlarged contact member 1030 is asymmetrically disposed with respect to the intersection of at least two struts of first strut 1010, second strut 1012, third strut 1014, and/or fourth strut 1016 such that first area 1034 or second area 1036 is asymmetric with respect to the intersection of first strut 1010, second strut 1012, third strut 1014, and fourth strut 1016 at node 1020. As shown in FIG. 10, first area 1034 and second area 1036 of asymmetric enlarged contact member 1030 extend outward from node 1020 in one direction, while asymmetric enlarged contact member 1030 is absent in the opposite direction from node 1020. With this arrangement, asymmetric enlarged contact member 1030 may provide a larger surface area for a contact surface of an implant in a particular location and/or direction on the implant.

In an exemplary embodiment, asymmetric enlarged contact member 1030 may have an approximately semi-circular or partially rounded shape. The semi-circular or partially rounded shape of asymmetric enlarged contact member 1030 shown in FIG. 10 fans outward in an approximately radial direction from node 1020 such that outer perimeter edge 1032 defines the semi-circular or partially rounded shape. In this embodiment, asymmetric enlarged contact member 1030 extends away from first strut 1010 and third strut 1014 in one direction from node 1020 so as to define an approximately fan-shaped semi-circular shape.

With regard to the shapes of enlarged contact members shown in the previous embodiments, including the shapes shown in FIGS. 5 through 10 described above, it should be understood that other shapes may also be provided, including, but not limited to, geometric and non-geometric or irregular shapes.

FIGS. 5 through 10 illustrate embodiments of an exemplary enlarged contact member. It should be understood that an implant can include any number of enlarged contact members with substantially similar configurations, as well as a combination of different configurations according to the previous embodiments. Implants according to the embodiments described herein may include enlarged contact members that are disposed at various nodes of intersection between two or more struts of a plurality of struts, including outer struts, inner struts, and/or a combination of both across various portions of the contact surfaces of the implant. With this configuration, an implant can be configured with enlarged contact members at selected locations across the contact surfaces of the implant as desired for a particular type or configuration of implant.

In some embodiments, an implant may be provided with bone contacting elements or struts that have a cross-sectional profile configured to assist with improved bone contact. As previously described, the approximately rounded or circular cross-sectional shape of bone contacting elements or struts may apply unwanted stress to bone in areas where the bone contacting elements of the implant are in direct contact with the bone. For example, FIGS. 11 and 12 illustrate an example of a prior art strut having an approximately rounded or circular cross-sectional shape.

Figure 11:
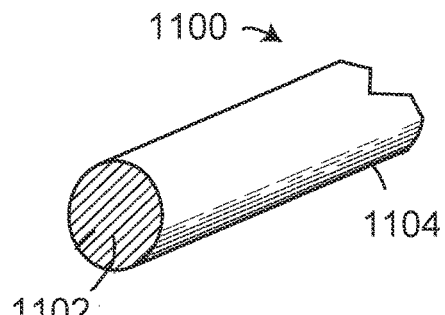
FIG. 11 is a schematic view of a prior art strut with a circular cross-sectional shape.
Figure 12:
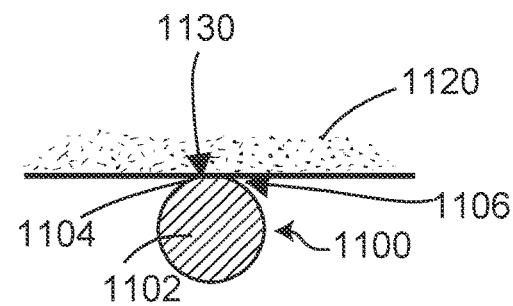
FIG. 12 is a schematic view of the prior art strut of FIG. 11 in contact with a bone.

As shown in FIG. 11, strut 1100 has an approximately rounded or circular cross-sectional shape 1102 and a cylindrical outer surface 1104. Strut 1100 is placed in contact with a bone, as shown in FIG. 12. Because of the rounded or circular cross-sectional shape 1102 of strut 1100, only a small portion of cylindrical outer surface 1104 is in direct contact with the outer surface of bone 1120. For example, in FIG. 12, contact area 1130 between cylindrical outer surface 1104 of strut 1100 and bone 1120 is a single point 1106, e.g., a tangent to rounded or circular cross-sectional shape 1102 of strut 1100, that forms a line extending along the length of strut 1100 in contact with bone 1120. Such a small contact area can place unwanted stress and force to bone 1120 along contact area 1130.

FIGS. 13 through 16 illustrate various embodiments of cross-sectional shapes for a strut of an implant that can assist with dissipating force and stress over a larger contact area with a bone of a patient.

Figure 13:
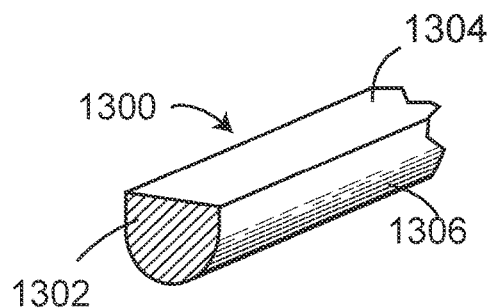
FIG. 13 is a schematic isometric view of a strut with a flattened cross-sectional shape, according to an embodiment.

Referring now to FIG. 13, an exemplary embodiment of a flattened strut 1300 has an inverted semi-circular dome shape 1302. In this embodiment, flattened strut 1300 includes a first portion having a rounded or semi-circular cross-sectional shape and a second portion having a generally flat shape. As shown in FIG. 13, flat surface 1304 of flattened strut 1300 is disposed along a top portion of flattened strut 1300 and semi-cylindrical outer surface 1306 extends from the top portion around the remaining portion of flattened strut 1300 to form the inverted semi-circular dome shape 1302.

Figure 14:
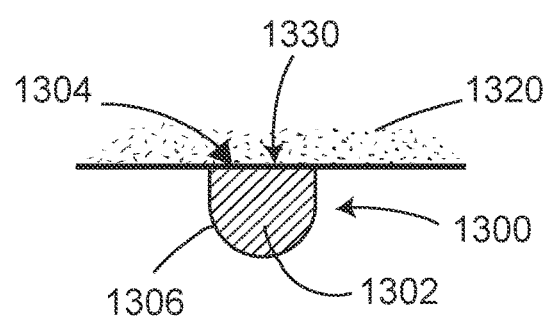
FIG. 14 is a schematic view of the strut of FIG. 13 in contact with a bone.

Flat surface 1304 of flattened strut 1300 provides a larger surface area for contact with a bone of a patient. As shown in FIG. 14, flat surface 1304 of flattened strut 1300 is in direct contact with the outer surface of bone 1320 along contact area 1330. In this embodiment, contact area 1330 extends across the lateral width of flattened strut 1300 and corresponds with the area of flat surface 1304 on the top portion of flattened strut 1300. With this configuration, contact area 1330 of flattened strut 1300 is significantly larger than contact area 1130 provided by point 1106 in the prior art strut 1100, described above.

Figure 15:
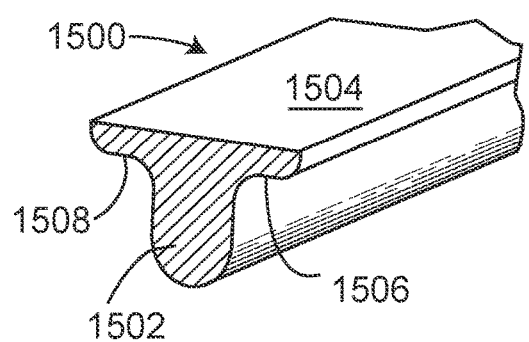
FIG. 15 is a schematic isometric view of a strut with a flattened cross-sectional shape, according to another embodiment.
Figure 16:
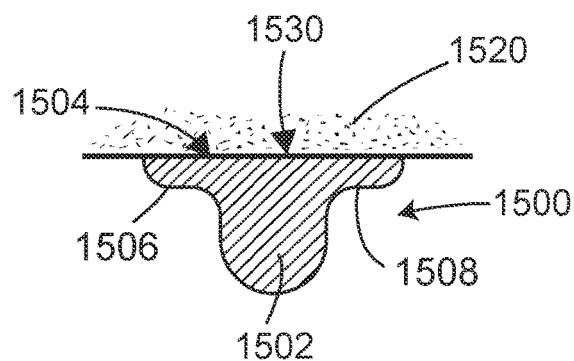
FIG. 16 is a schematic view of the strut of FIG. 15 in contact with a bone.

Referring now to FIG. 15, another exemplary embodiment of a flattened strut 1500 has an inverted bell shape 1502. In this embodiment, flattened strut 1500 includes a first portion having a rounded or semi-circular cross-sectional shape, two portions on either side of the first portion that flare outward to form a generally convex contour, and a third portion having a generally flat shape. As shown in FIG. 15, flat surface 1504 of flattened strut 1500 is disposed along a top portion of flattened strut 1500 and a semi-cylindrical outer surface extends from an opposite bottom portion and flares outward to form a generally convex contoured surface on either side of the bottom portion. The flared-out portions on the sides include a first wing 1506 and a second wing 1508 disposed on opposite sides of flat surface 1504. Together, the semi-cylindrical outer surface on the bottom portion, the flared first wing 1506 and flared second wing 1508, and flat surface 1504 on the top portion of flattened strut 1500 form the inverted bell shape 1502.

Flat surface 1504 of flattened strut 1500 provides a larger surface area for contact with a bone of a patient. As shown in FIG. 15, flat surface 1504 of flattened strut 1500 is in direct contact with the outer surface of bone 1520 along contact area 1530. In this embodiment, contact area 1530 extends across the lateral width of flattened strut 1500 and corresponds with the area of flat surface 1504 on the top portion of flattened strut 1500. With this configuration, contact area 1530 of flattened strut 1500 is significantly larger than contact area 1130 provided by point 1106 in the prior art strut 1100, described above. Additionally, because of flared first wing 1506 and flared second wing 1508, flat surface 1504 is also wider than flat surface 1304 of flattened strut 1300 to provide contact area 1530 of flattened strut 1500 that is larger than contact area 1330 of flattened strut 1300.

It should be understood that other configurations of cross-sectional shapes with flat surfaces for struts that are configured to provide an enlarged contact area with a bone of a patient are possible according to the principles described above with reference to FIGS. 13-16.

Manufacturing and Materials

The various components of an implant may be fabricated from biocompatible materials suitable for implantation in a human body, including, but not limited to, metals (e.g., titanium or other metals), synthetic polymers, ceramics, and/or their combinations, depending on the particular application and/or preference of a medical practitioner.

Generally, the implant can be formed from any suitable biocompatible, non-degradable material with sufficient strength. Typical materials include, but are not limited to, titanium, biocompatible titanium alloys (e.g. γTitanium Alum inides, $Ti_6$—$Al_4$—V ELI (ASTM F 136), or $Ti_6$—$Al_4$—V (ASTM F 1108 and ASTM F 1472)) and inert, biocompatible polymers, such as polyether ether ketone (PEEK) (e.g. PEEK-OPTIMA®, Invibio Inc). Optionally, the implant contains a radiopaque marker to facilitate visualization during imaging.

In different embodiments, processes for making an implant can vary. In some embodiments, the entire implant may be manufactured and assembled via injection-molding, cast or injection molding, insert-molding, co-extrusion, pultrusion, transfer molding, overmolding, compression molding, 3-Dimensional (3-D) printing, dip-coating, spray-coating, powder-coating, porous-coating, milling from a solid stock material, and their combinations.

Referring now to FIGS. 17 through 20, an exemplary process of manufacturing an implant with enlarged contact members, according to any of the previous embodiments is illustrated. In this exemplary process, an additive manufacturing technique, for example, 3-D printing, is used to manufacture an implant with enlarged contact members. According to the exemplary process, an implant, for example, implant 500, described above, is printed in a substantially vertical direction. That is, the implant is printed in a direction starting at one end along the perimeter surface of the implant and continuing to add layers until forming the opposite end of the perimeter surface. The exemplary process described here is in contrast to printing in a substantially horizontal direction, which would be in a direction starting at the contact surface on one side of the implant (e.g., the top or bottom of the implant) and continuing to add layers until forming the contact surface on the opposite side of the implant.

With the exemplary process, each of the inferior and superior contact surfaces on opposite sides of the implant are formed in a substantially vertical direction such that each successive layer adds material to both the inferior and superior contact surfaces on opposite sides of the implant during the same pass.

Figures 17, 18:
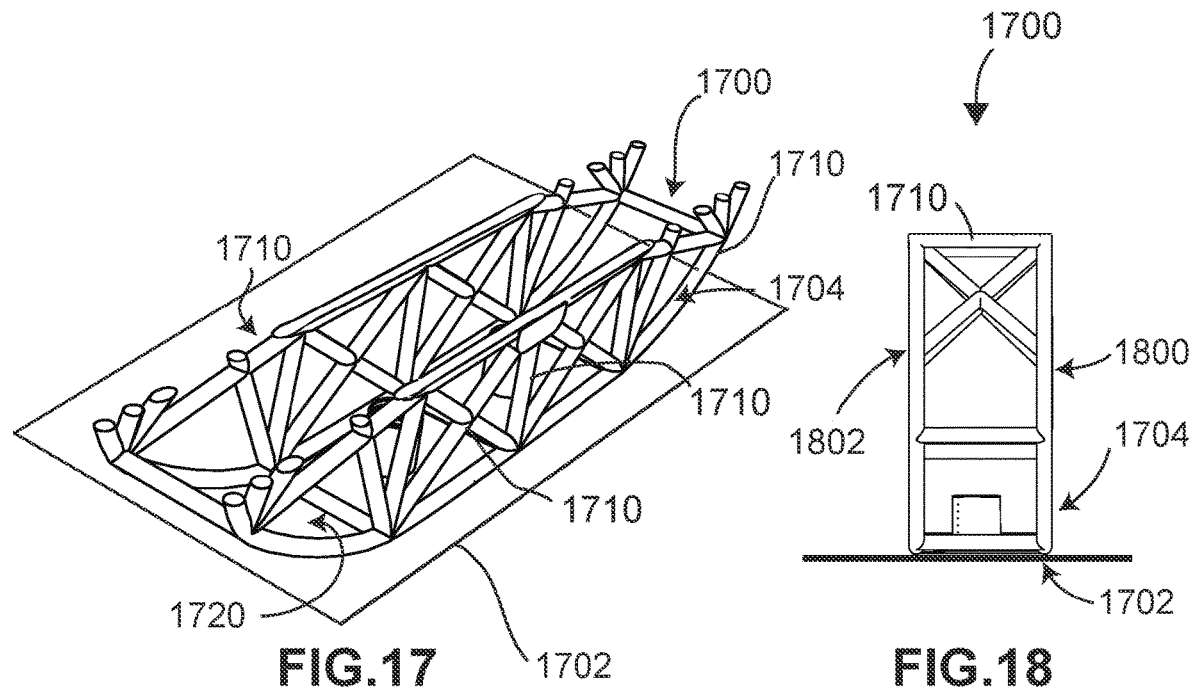
FIG. 17 is a schematic view of a process of manufacturing an implant, according to an embodiment.
FIG. 18 is a side view of the implant of FIG. 17 during manufacture.

Referring now to FIG. 17, an implant 1700 is shown in a partially printed condition during an exemplary manufacturing process. In this embodiment, the exemplary manufacturing process is an additive manufacturing process, for example, a 3-D printing process, that builds up material layer by layer to form the implant. The exemplary manufacturing process begins by additively manufacturing a first layer 1704 proximate to a base plate 1702. Base plate 1702 is a platform or other component that is configured to provide a surface for building the implant during the exemplary manufacturing process. As discussed above, in this exemplary process, implant 1700 is built in a substantially vertical direction. In this case, first layer 1704 is a portion of a perimeter surface of implant 1700. That is, implant 1700 has a substantially similar configuration as implant 500, described above, with a central core surrounded by an outer portion, opposite contact surfaces spaced from the central core, and a perimeter surface disposed approximately orthogonal to the contact surfaces and extending around the perimeter of the outer portion. With this configuration, the substantially vertical direction of manufacturing with the exemplary process results in first layer 1704 being a portion of the perimeter surface at one end of implant 1700.

During the exemplary manufacturing process, additional layers 1720 of material are built up in the vertical direction by multiple passes, with each pass adding material to first layer 1704 and subsequent additional layers to continue to form implant 1700. As shown in FIG. 17, implant 1700 is in a partially manufactured condition with first layer 1704 proximate base plate 1702 and a plurality of struts 1710 extending away from first layer 1704. In this embodiment, plurality of struts 1710 includes outer struts, substantially similar to outer struts 512, described above. As additional layers are formed during the exemplary manufacturing process, additional struts can be manufactured, including additional outer struts, inner struts, substantially similar to inner struts 514, described above, or a combination of outer and inner struts to form a lattice structure of implant 1700.

FIG. 18 illustrates a side view of implant 1700 during the exemplary manufacturing process shown in FIG. 17. In this embodiment, first layer 1704 is shown proximate to base plate 1702 and plurality of struts 1710 are shown in partial formation extending away from base plate 1702. In addition, during the substantially vertical direction of manufacturing, the contact surfaces on opposite sides of implant 1700 are formed in layers such that material is added to both sides during the same pass of the additive manufacturing process.

For example, in FIG. 18, implant 1700 includes a first contact surface 1800 and a second contact surface 1802 disposed on the opposite side of implant 1700. In this case, first contact surface 1800 can be an inferior surface and second contact surface can be a superior surface. During the additive manufacturing process, each successive layer adds material to both first contact surface 1800 and second contact surface 1802 on opposite sides of implant 1700 during the same pass.

Figures 19, 20:
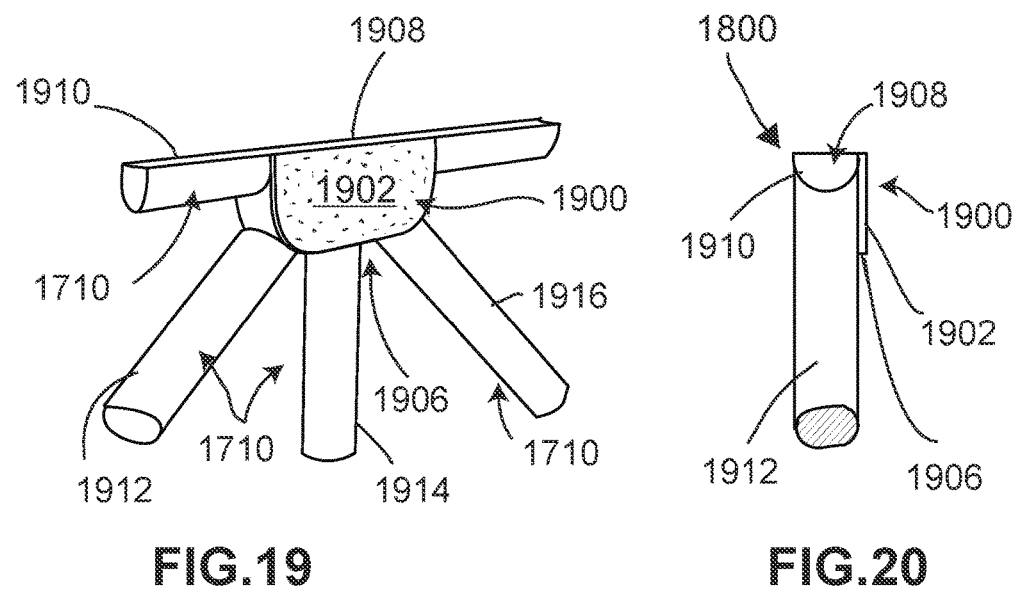
FIG. 19 is an enlarged view of an enlarged contact member of the implant of FIG. 17 during manufacture.
FIG. 20 is a side view of the enlarged contact member shown in FIG. 19.

In some embodiments, enlarged contact members, which may be substantially similar to any of the previous embodiments of enlarged contact members described above, can also be made during the exemplary process of making implant 1700. FIG. 19 illustrates a close-up view of an exemplary enlarged contact member 1900 that is additively manufactured on one or more of inferior and superior contact surfaces at nodes of intersection between plurality of struts 1710. In this embodiment, enlarged contact member 1900 is formed at a node of intersection between a first strut 1910, a second strut 1912, a third strut 1914, and a fourth strut 1916. As seen in FIG. 20, enlarged contact member 1900 is oriented so that a flattened surface 1902 of enlarged contact member 1900 is configured to face outward on first contact surface 1800 of implant 1700. With this arrangement, flattened surface 1902 of enlarged contact member 1900 is configured to confront a bone of a patient.

In some embodiments, enlarged contact members can be manufactured such that one end that is closer to the base plate is narrower than the other end that is disposed further from base plate. As shown in FIG. 19, enlarged contact member 1900 includes a first end 1906 that is disposed closer to base plate 1702. During the exemplary manufacturing process, first end 1906 of enlarged contact member 1900 is formed first and successive layers build up additional material to form enlarged contact member 1900. In some cases, as successive layers build up enlarged contact member 1900, enlarged contact member 1900 may become wider than first end 1906.

As shown in FIG. 19, first end 1906 is narrower than a second end 1908 that is disposed further from base plate 1702. That is, second end 1908 of enlarged contact member 1900 has a larger width than first end 1906 of enlarged contact member 1900. With successive layers of additive manufacturing, enlarged contact member 1900 widens from first end 1906 to second end 1908. This exemplary process can provide an asymmetrical shape to enlarged contact member 1900, for example, any of the asymmetrical shapes described above with reference to FIGS. 9 and 10 above. In addition, first end 1906 having a smaller width than second end 1908 can provide a more secure attachment to plurality of struts 1710 and may also permit the width of enlarged contact member 1900 to increase gradually to the width at second end 1908 during the additive manufacturing process.

In addition, the additive manufacturing process described above can provide texture to flattened surface 1902 of enlarged contact member 1900. The addition of material in successive layers to form enlarged contact member 1900 can provide surface irregularities that serve as a textured surface for flattened surface 1902 of enlarged contact member 1900. With this arrangement, the textured flattened surface 1902 of enlarged contact member 1900 may assist with providing greater adhesion in contact with a bone of a patient.

Thus, in some cases, the implant may be formed by additive manufacturing (e.g., 3-D printing) in an anatomical orientation. That is, the implant may be formed from the bottom up in its regular upright position, as it would be positioned within the body of the patient. However, in other cases, the implant may be formed by an additive manufacturing process in a non-anatomical orientation. For example, in some cases, the implant may be formed on its side, as discussed above. For instance, in some cases, the implant may be formed beginning with the anterior surface and concluding with the posterior surface. In some cases, the implant may be formed beginning with one lateral side and concluding with the opposing lateral side.

Provisions may be used to facilitate additive manufacturing in one or more particular orientations. For example, in some cases, additive manufacturing may be facilitated by the orientations of the struts. For example, in the orientation in which the implant is desired to be manufactured, the roof angle, i.e., the angle between the underside of a structural component and a horizontal plane, may be 30 degrees or greater. In some embodiments, the minimum roof angle may be 32 degrees.

Alternatively, or additionally, thin, vertically oriented elements, may be printed with the implant, but knocked out after the printing is completed. Such knock-out or punch-out elements may be utilized anywhere in the implent to facilitate manufacturing. In some embodiments, closely-spaced, paper-thin vertical elements may be printed as a supportive base in order to additively manufacture structures with a roof angle of less than 30 degrees. With the vertical elements so closely spaced, there is a small enough span between the vertical elements that the horizontal structures can be added despite having a roof angle smaller than 30 degrees. Because the vertical elements are so thin, they can be easily broken away from the completed implant after the additive manufacturing process has been complete. That is, the vertical elements can be "knock-outs" or "punch-out" elements that are removed after manufacturing. In some embodiments, implants may be provided that include one or more features disclosed in Sack, U.S. Patent Application Publication No. 2019/0151113, published on May 23, 2019, and entitled "Implant with Improved Flow Characteristics."

Figure 21:
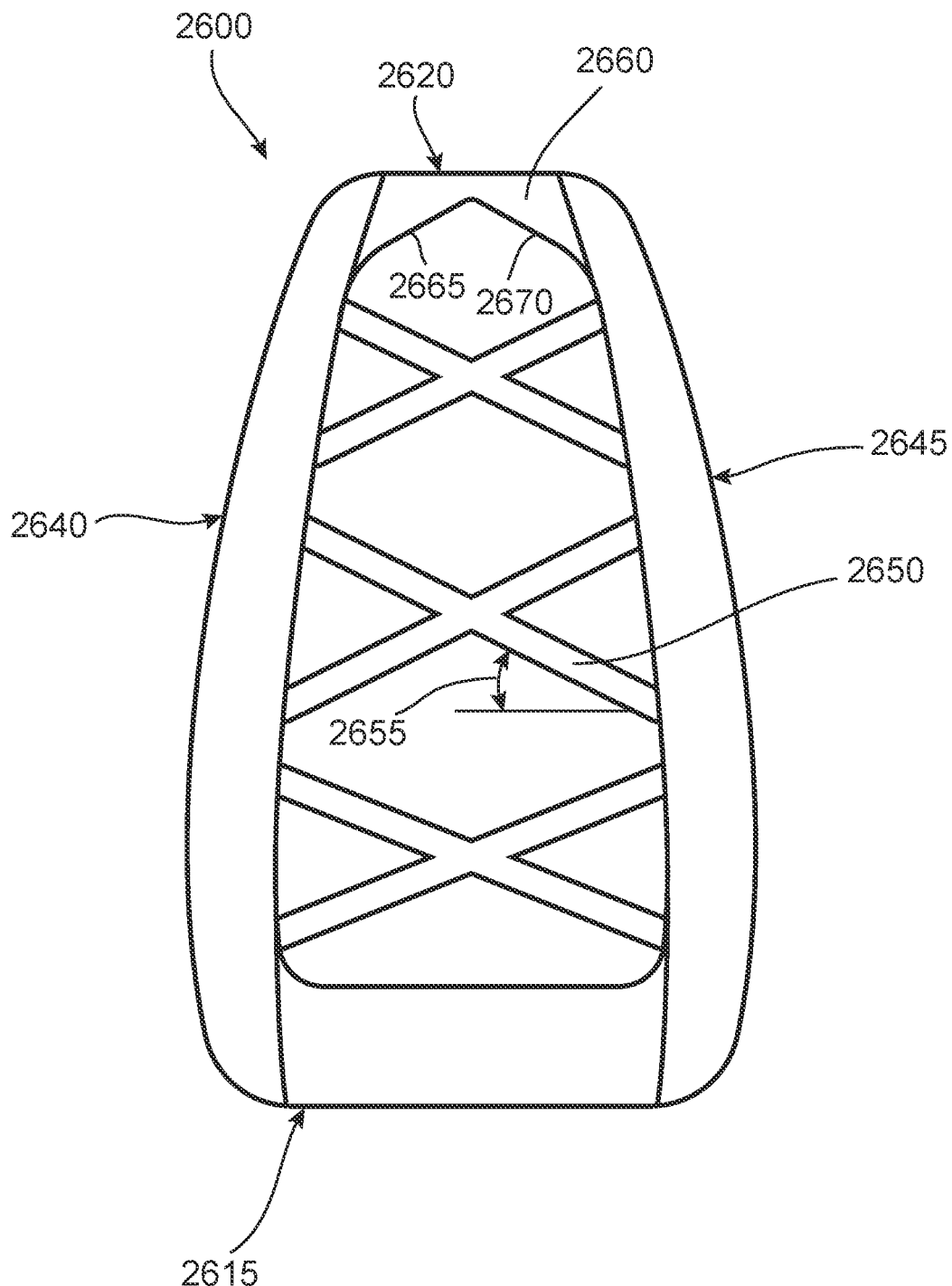
FIG. 21 is a schematic lateral view of another implant.

FIG. 21 is a lateral view of implant 2600 when oriented standing on an anterior side 2615 as it would be during the manufacturing process illustrated in FIG. 26. Implant 2600 includes structural features having roof angles that are a minimum of 30 degrees. As shown in FIG. 21, implant 2600 also includes a posterior side 2620. Further, implant 2600 may also include a superior surface 2640 and an inferior surface 2645. As shown in FIG. 21, implant 2600 may include a plurality of peripheral struts around the perimeter of implant 2600 that are arranged in X-shaped configurations. As shown in FIG. 21, first peripheral strut 2650 has a roof angle 2655. In some embodiments, roof angle 2655 may be 30 degrees or greater. For example, in some cases, roof angle 2655 may be approximately 32 degrees. In some embodiments, each of the peripheral struts may have roof angles of 30 degrees or greater. In some cases, the minimum roof angle of the peripheral struts may be approximately 32 degrees.

In addition, as also shown in FIG. 21, posterior structures extending in the superior-inferior direction, such as a posterior structure 2660, may have roof angles of 30 degrees or more. Posterior structure 2660 may have a first anterior-facing surface 2665 and a second anterior-facing surface 2670. As shown in FIG. 21, first anterior-facing surface 2665 and second anterior-facing surface 2670 may both have roof angles of 30 degrees or more. For example, in some cases, all structural elements extending in the superior-inferior direction may have a minimum roof angle of 30 degrees or more. For instance, the minimum roof angle may be approximately 32 degrees.

Figure 22:
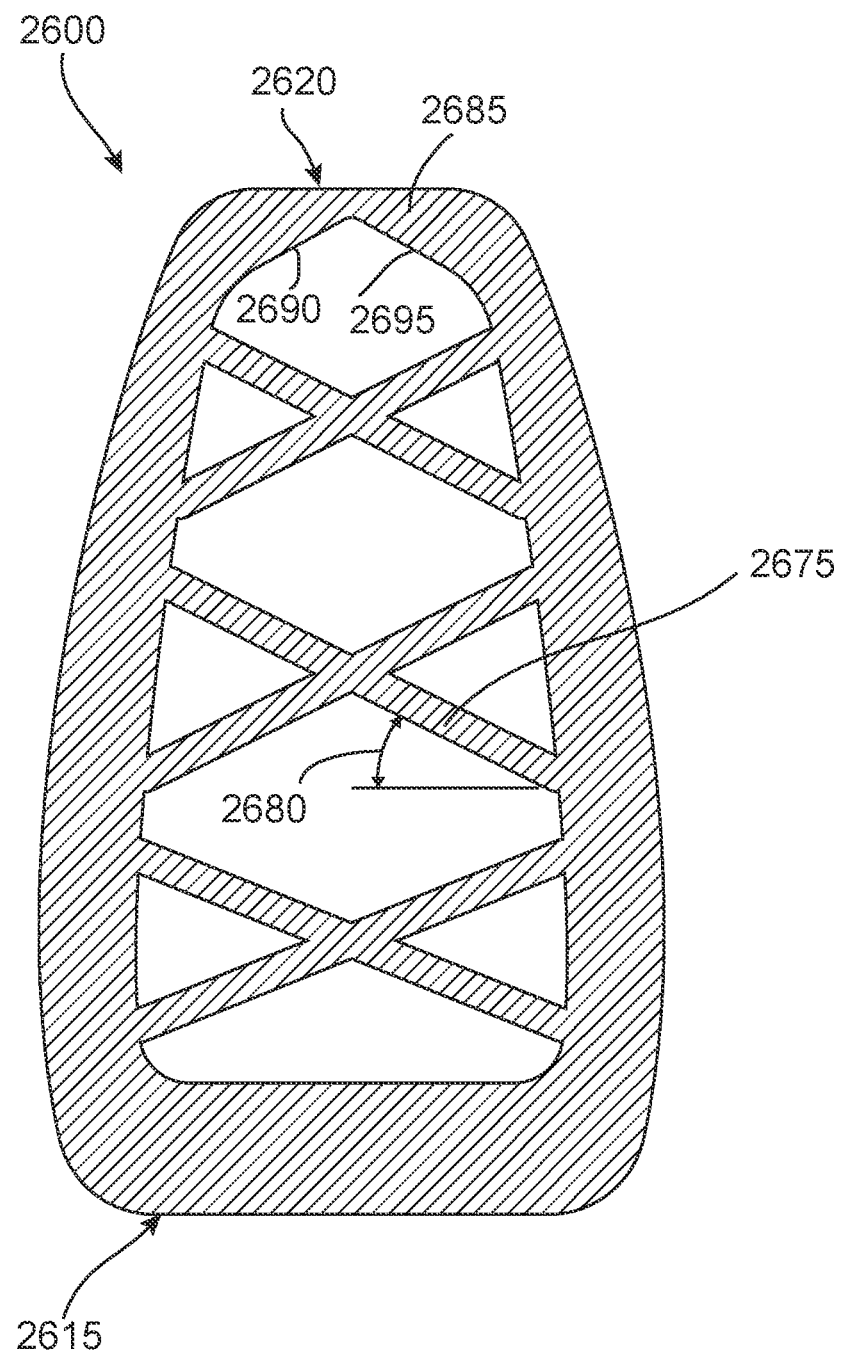
FIG. 22 is a schematic cross-sectional view of the implant shown in FIG. 21.

It will also be understood that, in addition to the peripheral structures, the internal structures of implant 2600 may also have minimum roof angles of 30 degrees or more. For example, as shown in FIG. 22, an internal strut 2675 may have a roof angle 2680. In some embodiments, roof angle 2680 may be 30 degrees or greater. For example, in some cases, roof angle 2680 may be approximately 32 degrees.

In addition, internal posterior structures, such as a posterior structure 2685, may have roof angles of 30 degrees or more. Posterior structure 2685 may have a first anterior-facing surface 2690 and a second anterior-facing surface 2695. As shown in FIG. 22, first anterior-facing surface 2690 and second anterior-facing surface 2695 may both have roof angles of 30 degrees or more. For example, in some cases, all structural elements extending in the superior-inferior direction may have a minimum roof angle of 30 degrees or more. For instance, the minimum roof angle may be approximately 32 degrees.

While various embodiments have been described, the description is intended to be exemplary, rather than limiting, and it will be apparent to those of ordinary skill in the art that many more embodiments and implementations are possible that are within the scope of the embodiments. Although many possible combinations of features are shown in the accompanying figures and discussed in this detailed description, many other combinations of the disclosed features are possible. Any feature of any embodiment may be used in combination with or substituted for any other feature or element in any other embodiment unless specifically restricted. Therefore, it will be understood that any of the features shown and/or discussed in the present disclosure may be implemented together in any suitable combination. Accordingly, the embodiments are not to be restricted except in light of the attached claims and their equivalents. Also, various modifications and changes may be made within the scope of the attached claims.

What is claimed is:

1. An intervertebral implant comprising:
   a body having an open lattice structure formed by a plurality of elongate struts, including a first strut and a second strut;

the first strut having a first longitudinal length and a first lateral width, the first longitudinal length being longer than the first lateral width;

the second strut having a second longitudinal length and a second lateral width, the second longitudinal length being longer than the second lateral width;

the body including a contact surface configured to confront a bone plate;

the contact surface including a node defined by an intersection of the first strut and the second strut;

wherein the implant includes an enlarged contact member disposed at the node defined by the intersection of the first strut and the second strut;

wherein the enlarged contact member has a substantially flattened outer-facing surface forming part of the contact surface;

wherein the enlarged contact member has an outer perimeter edge that extends beyond the node defined by the intersection of the first strut and the second strut; and wherein at least a portion of the first strut and at least a portion of the second strut extend inward from the enlarged contact member toward a central core of the body.

2. The intervertebral implant according to claim 1, wherein the contact surface is a superior surface configured to confront an upper bone plate.

3. The intervertebral implant according to claim 1, wherein the contact surface is an inferior surface configured to confront a lower bone plate.

4. The intervertebral implant according to claim 1, wherein the enlarged contact member is asymmetrically disposed with respect to the intersection of the first strut and the second strut.

5. The intervertebral implant according to claim 1, wherein at least one of the first strut and the second strut includes a curved arch portion.

6. The intervertebral implant according to claim 1, wherein at least one of the first strut and the second strut has a flattened cross-sectional shape.

7. An intervertebral implant comprising:

a body having a lattice structure formed by a plurality of elongate struts, including a first strut and a second strut;

the first strut having a first longitudinal length and a first lateral width, the first longitudinal length being longer than the first lateral width;

the second strut having a second longitudinal length and a second lateral width, the second longitudinal length being longer than the second lateral width;

the body including a superior surface and an inferior surface;

the superior surface configured to confront an upper bone plate;

the inferior surface configured to confront a lower bone plate;

at least one of the superior surface and the inferior surface including a node defined by an intersection of the first strut and the second strut;

wherein the implant includes an enlarged contact member disposed at the node defined by the intersection of the first strut and the second strut;

wherein the enlarged contact member has a substantially flattened outer-facing surface forming part of the outer portion of the body;

wherein the enlarged contact member has an outer perimeter edge that extends beyond the node defined by the intersection of the first strut and the second strut; and wherein the enlarged contact member has an oblong shape.

8. The intervertebral implant according to claim 7, wherein at least one of the first strut and the second strut includes a curved arch portion.

9. The intervertebral implant according to claim 7, wherein the substantially flattened surface is oriented along one of the superior surface and the inferior surface of the intervertebral implant.

10. The intervertebral implant according to claim 7, wherein the oblong-shaped enlarged contact member has a long axis that is oriented at an angle with respect to at least one of the first strut and the second strut.

11. The intervertebral implant according to claim 7, further comprising a plurality of enlarged contact members on at least one of the superior surface and the inferior surface of the intervertebral implant.

12. The intervertebral implant according to claim 7, wherein at least one of the first strut and the second strut has a flattened cross-sectional shape.

13. The intervertebral implant according to claim 12, wherein the flattened cross-sectional shape of the at least one of the first strut and the second strut is oriented along one of the superior surface and the inferior surface of the intervertebral implant.

14. An intervertebral implant comprising:

a body having an open lattice structure formed by a plurality of elongate struts, including a first strut and a second strut;

the first strut having a first longitudinal length and a first lateral width, the first longitudinal length being longer than the first lateral width;

the second strut having a second longitudinal length and a second lateral width, the second longitudinal length being longer than the second lateral width;

the implant including a node defined by an intersection of the first strut and the second strut;

wherein the implant includes an enlarged contact member disposed at the node defined by the intersection of the first strut and the second strut;

wherein the enlarged contact member has a substantially flattened outer-facing surface forming part of an outer portion of the body;

wherein the enlarged contact member has an outer perimeter edge that extends beyond the node defined by the intersection of the first strut and the second strut; and wherein at least one of the first strut and the second strut includes a curved arch portion.

15. The intervertebral implant according to claim 14, wherein the enlarged contact member has an oblong shape aligned at an angle with respect to at least one of the first strut and the second strut.

16. The intervertebral implant according to claim 14, wherein the contact surface is a superior surface configured to confront an upper bone plate.

17. The intervertebral implant according to claim 14, wherein the contact surface is an inferior surface configured to confront a lower bone plate.

18. The intervertebral implant according to claim 14, wherein the enlarged contact member is asymmetrically disposed with respect to the intersection of the first strut and the second strut.

19. The intervertebral implant according to claim 14, wherein at least one of the first strut and the second strut has a flattened cross-sectional shape.

20. The intervertebral implant according to claim 14, wherein at least a portion of the first strut and at least a portion of the second strut extend inward from the enlarged contact member toward the central core of the body.

* * * * *